US007033595B1

(12) United States Patent
Sanders et al.

(10) Patent No.: US 7,033,595 B1
(45) Date of Patent: Apr. 25, 2006

(54) PSEUDOTYPED RETROVIRUSES AND STABLE CELL LINES FOR THEIR PRODUCTION

(75) Inventors: David A. Sanders, West Lafayette, IN (US); Richard J. Kuhn, West Lafayette, IN (US); Scott A. Jeffers, West Lafayette, IN (US); Curtis M. Sharkey, Lafayette, IN (US); Cynthia L. North, Lafayette, IN (US); Michael A. Fishbach, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/762,224

(22) PCT Filed: Aug. 4, 1999

(86) PCT No.: PCT/US99/17702

§ 371 (c)(1), (2), (4) Date: Jul. 30, 2001

(87) PCT Pub. No.: WO00/08131

PCT Pub. Date: Feb. 17, 2000

Related U.S. Application Data

(60) Provisional application No. 60/095,242, filed on Aug. 4, 1998, provisional application No. 60/112,405, filed on Dec. 15, 1998.

(51) Int. Cl.
*A61K 39/12* (2006.01)

(52) U.S. Cl. ................................ 424/199.1; 424/218.1

(58) Field of Classification Search ............. 435/320.1; 536/23.72; 424/199.1, 218.1
See application file for complete search history.

(56) References Cited

U.S. PATENT DOCUMENTS

| | | | | |
|---|---|---|---|---|
| 4,912,030 | A | 3/1990 | Weiss et al. | 435/5 |
| 5,185,440 | A | 2/1993 | Davis et al. | 536/237.2 |
| 5,278,056 | A | 1/1994 | Bank et al. | 435/172.3 |
| 5,491,084 | A | 2/1996 | Chalfie et al. | 435/189 |
| 5,503,974 | A | 4/1996 | Gruber et al. | 435/5 |
| 5,512,421 | A | 4/1996 | Burns et al. | 435/320 |
| 5,591,624 | A | 1/1997 | Barber et al. | 435/240.2 |
| 5,681,746 | A | 10/1997 | Bodner et al. | 435/350 |
| 5,723,287 | A | 3/1998 | Russell et al. | 435/5 |
| 5,723,333 | A | 3/1998 | Levine et al. | 435/69.1 |
| 5,739,018 | A | 4/1998 | Miyanohara et al. | 435/172.3 |
| 5,747,243 | A | 5/1998 | Gruber et al. | 435/5 |
| 5,750,396 | A | 5/1998 | Yang et al. | 435/357 |
| 5,910,434 | A | 6/1999 | Rigg et al. | 435/172.3 |

OTHER PUBLICATIONS

Will, C., et al., *Marburg Virus Gene 4 Encodes the Virion Membrane Protein, a Type I Transmembrane Glycoprotein*, J. of Virology, 67:3:1203-1210 (1993).

Sanchez, A., et al., *Sequence Analysis of the Ebola Virus Genome: Organization, Genetic Elements, and Comparison with the Genome of Marburg Virus*, Virus Research, 29:215-240 (1993).

Lopez, S., et al., *Nucleocapsid-Glycoprotein Interactions Required for Assembly of Alphaviruses*, J. of Virology, 68:3:1316-1323 (1994).

Riviere, I, et al., *Effects of Retroviral Vector Design on Expression of Human Adenosine Deaminase in Murine Bone Marrow Transplant Recipients Engrafted with Genetically Modified Cells*, Proc. Nat'l. Acad. Sci. USA, 92:6733-6737 (1995).

Sharma, S., et al., *Efficient Infection of a Human T-Cell Line and of Human Primary Peripheral Blood Leukocytes with a Pseudotyped Retrovirus Vector*, Proc. Nat'l Acad. Sci. USA, 93:21:11842-11847 (1996).

Ory, D. S., et al., *A Stable Human-Derived Packaging Cell Line for Production of High Titer Retrovirus/Vesicular Stomatitis Virus G Pseudotypes*, Proc. Nat'l. Acad. Sci. USA, 93:11400-11406 (1996).

Kuhn, R. J., et al., *Chimeric Sindbis-Ross River Viruses to Study Interactions Between Alphavirus Nonstructural and Structural Regions*, J. of Virology, 70:11:7900-7909 (1996).

(Continued)

*Primary Examiner*—Jeffrey S. Parkin
(74) *Attorney, Agent, or Firm*—Mueting, Raasch & Gebhardt, P.A.

(57) ABSTRACT

Cells that produce inventive pseudotyped retroviruses having a broad host range have been produced. In one aspect of the invention, the cells produce retroviruses pseudotyped with at least two different viral glycoproteins, such as togaviral glycoproteins. In alternative embodiments, the cells produce retroviruses pseudotyped with filoviral glycoproteins. Methods of producing the above-described cells, as well as the pseudotyped retroviruses thus produced, are also provided. In other embodiments, methods of screening agents effective in blocking viral entry into a cell, including filoviral entry or entry of viruses having at least two different viral glycoproteins disposed in their lipid bilayer, such as togaviruses, are provided. Moreover, methods of using the inventive pseudotyped retroviruses for introducing nucleotide sequences into target cells, and kits for forming the inventive pseudotyped retroviruses, are also provided.

23 Claims, 6 Drawing Sheets

OTHER PUBLICATIONS

Takada, A., et al., *A System for Functional Analysis of Ebola Virus Glycoprotein*, Proc. Nat'l. Acad. Sci. USA, 94:14764-14769 (1997).

Grignani, F., et al., *High-Efficiency Gene Transfer and Selection of Human Hematopoietic Progenitor Cells with a Hybrid EBV/Retroviral Vector Expressing the Green Fluorescence Protein*, Cancer Research, 58:14-19 (1998).

Yang, Z., et al., *Distinct Cellular Interactions of Secreted and Transmembrane Ebola Virus Glycoproteins*, Science, 279:1034-1037 (1998).

Wool-Lewis, R. and Bates, P., *Characterization of Ebola Virus Entry by Using Pseudotyped Viruses: Identification of Receptor-Deficient Cell Lines*, J. of Virology, 72:4:3155-3160 (1998).

Hatzhoannou, T., et al., *Incorporation of Fowl Plague Virus Hemagglutinin into Murine Leukemia Virus Particles and Analysis of the Infectivity of the Pseudotyped Retroviruses*, J. of Virology, 72:6:5313-5317 (1998).

Blanton et al. "Plasmid transfection and retroviral transduction of porcine muscle cells for cell-mediated gene transfer." *J. Anim. Sci.* 2000;78(4):909-18.

Current Protocols in Molecular Biology, Ausubel et al. eds. 1988. Table of Contents.

Faragher et al. "Genome Sequences of a Mouse-Avirulent and a Mouse-Virulent Strain of Ross River Virus" *Virology* 1988;163:509-526.

Jeffers et al. "Covalent modifications of the ebola virus glycoprotein." *J. Virol.* 2002;76(24):12463-72.

Kang et al. "In vivo gene transfer using a nonprimate lentiviral vector pseudotyped with Ross River Virus glycoproteins." *J Virol.* 2002;76(18):9378-88.

Kuhn et al. "Infectious RNA Transcripts from Ross River Virus cDNA Clones and the Construction and Characterization of Defined Chimeras with Sindbis Virus" *Virology* 1991;182:430-441.

Lodge R, et al. "Two distinct oncornaviruses harbor an intracytoplasmic tyrosine-based basolateral targeting signal in their viral envelope glycoprotein." *J Virol.* 1997;71(7):5696-702.

Markowitz et al. "A safe packaging line for gene transfer: separating viral genes on two different plasmids." *J Virol.* 1988;62(4):1120-4.

Marsh et al. "Virus entry into animal cells." *Adv Virus Res.* 1989;36:107-51.

Molecular Cloning, A Laboratory Manual, Cold Spring Harbor Laboratory 1989. Table of Contents.

Morgenstern et al. "A series of mammalian expression vectors and characterisation of their expression of a reporter gene in stably and transiently transfected cells." *Nucleic Acids Res.* 1990;18(4):1068.

National Center for Biotechnology Information, National Library of Medicine, National Institutes of Health, GenBank Locus EVU23187 bp RNA, Accession No. U23187, "Zaire Ebola virus Mayinga strain glycorotein (GP) gene, compete cds." [online]. Bethesda, MD (Feb. 8, 2003).<URL: http://www.ncbi.nlm.nih.gov/entrez/query.fcgi?cmd=Retrieve&db=nucleotide&list_uids=10, (3 pgs.).

National Center for Biotechnology Information, National Library of Medicine, National Institutes of Health, GenBank Locus MVREPCYC 2845 bp DNA, Accession No. Z12132, "Marburg virus genes for vp35, vp40, vp30 vp24, glycoprotein, nucleoprotein, polymerase," [online]. Bethesda, MD (Feb. 10, 2003).<URL: http://www.ncbi.nlm.nih.gov/entrez/viewer.fcgi?cmd=&txt=&save=&cfm=&query_key=2&db=nucleotide&Extrafeat=-1&vie (3 pgs.).

National Center for Biotechnology Information, National Library of Medicine, National Institutes of Health, GenBank Locus MVREPCYC 19104 bp DNA, Accession No. MVREPCYC, "Marburg virus genes fro vp35,vp40, vp30, vp24, glycoprotein, nucleoprotein, polymerase," [online]. Bethesda, MD (Aug. 26, 2002).<URL: http://www.ncbi.nlm.nih.gov/entrez/query.fcgi?cmd=Retrieve&db=Nucleotide&list_uids=5, (11 pgs.).

Pear et al. "Production of high-titer helper-free retroviruses by transient transfection" *Proc Natl Acad Sci U S A.* 1993;90(18):8392-6.

Prasher et al. "Primary structure of the Aequorea victoria green-fluorescent protein." *Gene.* 1992;111(2):229-33.

Retroviruses, Cold Spring Harbor Laboratory Press, ed. By Coffin et al. 1997;444.

Sanders DA. "No false start for novel pseudotyped vectors." *Curr Opin Biotechnol.* 2002;13(5):437-42.

Sanes et al. "Use of a recombinant retrovirus to study post-implantation cell lineage in mouse embryos." *EMBO J.* 1986;5(12):3133-42.

Smith et al. "Putative receptor binding sites on alphaviruses as visualized by cryoelectron microscopy." *Proc Natl Acad Sci U S A.* 1995;92(23):10648-52.

Strauss et al. "The alphaviruses: gene expression, replication, and evolution." *Microbiol Rev.* 1994;58(3):491-562.

Taylor, G. M. and D. A. Sanders. 1999. The role of the membrane-spanning-domain sequence in glycoprotein-mediated membrane fusion. *Mol. Biol. Cell* 10:2803-2815.

Taylor et al. "Fv-4: identification of the defect in Env and the mechanism of resistance to ecotropic murine leukemia virus." *J Virol.* 2001;75(22):11244-8.

Van Beveren et al. "Nucleotide sequence of the genome of a murine sarcoma virus." *Cell* 1981;27(1 Pt 2):97-108.

gpnlslacZ     SafeRR-
              nlslacZ

66K —

45K —

31K —

SEQUENCE LISTING

```
<160> NUMBER OF SEQ ID NOS: 8

<210> SEQ ID NO 1
<211> LENGTH: 2958
<212> TYPE: DNA
<213> ORGANISM: Ross River virus

<400> SEQUENCE: 1
atgtctgccg cgctgatgat gtgtatcctt gccaacacct ctttcccctg ctcatcacct      60
ccctgctacc cctgctgcta cgaaaaacag ccagaacaga cactgcggat gctggaagac     120
aatgtgaata gaccagggta ctatgagcta ctggaagcgt ccatgacatg cagaaacaga     180
tcacgccacc gccgtagtgt aacagagcac ttcaatgtgt ataaggctac tagaccgtac     240
ttagcgtatt gcgctgactg tggggacggg tacttctgct atagcccagt tgctatcgag     300
aagatccgag atgaggcgtc tgacggcatg ctcaagatcc aagtctccgc ccaaataggt     360
ctggacaagg caggtaccca cgcccacacg aagatccgat atatggctgg tcatgatgtt     420
caggaatcta agagagattc cttgagggtg tacacgtccg cagcgtgctc tatacatggg     480
acgatgggac acttcatcgt cgcacattgt ccgccaggcg actacctcaa ggtttcgttc     540
gaggacgcag attcacacgt gaaggcatgt aaggtccaat acaagcacga cccattgccg     600
gtgggtagag agaagttcgt ggttagaccc cactttggcg tagagctgcc atgcacctca     660
```

```
taccagctga caacagctcc caccgacgag gagatcgaca tgcacacacc gccagatata    720
ccggatcgca ccctgctatc acagacggcg ggcaacgtca aataacagc aggcggcagg     780 actatcaggt acaattgtac ctgtggccgt gacaacgtag gcactaccag tactgacaag    840
accatcaaca catgcaagat tgaccaatgc catgctgccg ttaccagcca tgacaaatgg    900
caatttacct ctccatttgt tcccagggct gatcagacag ctaggagggg caaagtgcat    960
gttccattcc ctttgactaa cgtcacctgc cgagtgccgt tggctcgagc gccggatgtc    1020
acctatggta agaaggaggt gaccctgaga ttacacccag atcatccgac gctcttctcc    1080
tataggagtt taggagccga accgcacccg tacgaggagt gggttgacaa gttctctgag    1140
cgcatcatcc cagtgacgga agaagggatt gagtaccagt ggggcaacaa cccgccggtc    1200
cgcctatggg cgcaactgac gaccgagggc aaacccatg gctggccaca tgaaatcatt     1260
cagtactatt atggactata ccccgccgcc accattgccg cagtatccgg ggcgagtctg    1320
atggccctcc taactctagc ggccacatgc tgcatgctgg ccaccgcgag gagaaagtgc    1380
ctaacaccat acgccttgac gccaggagcg gtggtaccgt tgacactggg gctgctttgc    1440
tgcgcaccga gggcgaacgc agcatcattc gctgagacta tggcatatct gtgggacgag    1500
aacaaaaccc tcttttggat ggaattcgcc gccccagccg cagcgcttgc tttgctggca    1560
tgctgtatca aaagcctgat ctgctgttgt aagccatttt ctttttagt gttactgagc     1620 ctgggagcct ccgcaaaagc ttacgagcac acagccacaa ttccgaatgt ggtggggttc    1680
ccgtataagg ctcacattga aaggaatggc ttctcgccca tgactctgca gcttgaagtg    1740
gtggagacaa gcttggaacc cacacttaac ctggagtaca ttacctgcga atacaagacg    1800
gtggtcccct tcgccattcat caaatgttgc ggaacatcag aatgctcatc caaggagcag    1860
ccagactacc aatgcaaggt gtacacgggt gtatacccat tcatgtgggg tggagcctac    1920
tgtttctgcg actccgagaa cacgcagctc agcgaggcct atgtcgacag gtcagacgtt    1980
tgcaaacatg atcacgcatc ggcctacaag gcacacacgg cctctctaaa agcaacaatc    2040
aggatcagtt atggcaccat caaccagacc accgaggcct tcgttaatgg tgaacacgcg    2100
gtcaacgtgg gcggaagcaa gttcatcttt ggaccgatct caacagcttg gtcaccgttc    2160
gacaataaaa ttgtcgtgta taagatgat gtctacaacc aggacttccc accctacgga     2220
tcaggccagc cgggtagatt cggagacatt cagagcagga cagtggagag caaagacttg    2280
tatgccaaca cggccctaaa actctcaaga ccatcacccg gggttgtgca tgtgccatac    2340
acgcagacac catccggatt taaatattgg ctgaaggaga aaggatcttc attgaataca    2400 aaggccccctt ttggctgcaa gataaagacc aatccagtca gagccatgga ttgtgcagtt    2460
ggcagtatac ctgtgtcgat ggacatacct gacagtgcat tcacacgagt ggtagatgcc    2520
ccggctgtaa cagacctgag ctgccaggta gtggtctgta cacactcctc cgatttcgga    2580
ggagttgcca cattgtctta caaaacggac aaacccggca agtgcgctgt ccactcacat    2640
tccaacgtcg caacgttgca agaggcgacg gtggatgtca aggaggatgg caaggtcaca    2700
gtgcactttt ccacggcgtc cgcctccccg gccttcaaag tgtccgtctg tgacgcaaaa    2760
acaacgtgca cggcggcgtg cgagcctcca aaagaccaca tcgtcccta tggggcgagc    2820 cataacaacc aggtctttcc ggacatgtca ggaactgcga tgacgtgggt gcagaggctg    2880
gccagtgggt taggtgggct ggctctcatc gcggtggttg tgctggtctt ggtaacctgc    2940
ataacaatgc gtcggtaa                                                 2958
```

-continued

<210> SEQ ID NO 2
<211> LENGTH: 985
<212> TYPE: PRT
<213> ORGANISM: Ross River virus

<400> SEQUENCE: 2

```
Met Ser Ala Ala Leu Met Met Cys Ile Leu Ala Asn Thr Ser Phe Pro
1               5                   10                  15

Cys Ser Ser Pro Pro Cys Tyr Pro Cys Cys Tyr Glu Lys Gln Pro Glu
            20                  25                  30

Gln Thr Leu Arg Met Leu Glu Asp Asn Val Asn Arg Pro Gly Tyr Tyr
        35                  40                  45

Glu Leu Leu Glu Ala Ser Met Thr Cys Arg Asn Arg Ser Arg His Arg
    50                  55                  60

Arg Ser Val Thr Glu His Phe Asn Val Tyr Lys Ala Thr Arg Pro Tyr
65                  70                  75                  80

Leu Ala Tyr Cys Ala Asp Cys Gly Asp Gly Tyr Phe Cys Tyr Ser Pro
                85                  90                  95

Val Ala Ile Glu Lys Ile Arg Asp Glu Ala Ser Asp Gly Met Leu Lys
            100                 105                 110

Ile Gln Val Ser Ala Gln Ile Gly Leu Asp Lys Ala Gly Thr His Ala
        115                 120                 125

His Thr Lys Ile Arg Tyr Met Ala Gly His Asp Val Gln Glu Ser Lys
    130                 135                 140

Arg Asp Ser Leu Arg Val Tyr Thr Ser Ala Ala Cys Ser Ile His Gly
145                 150                 155                 160

Thr Met Gly His Phe Ile Val Ala His Cys Pro Pro Gly Asp Tyr Leu
                165                 170                 175

Lys Val Ser Phe Glu Asp Ala Asp Ser His Val Lys Ala Cys Lys Val
            180                 185                 190

Gln Tyr Lys His Asp Pro Leu Pro Val Gly Arg Glu Lys Phe Val Val
        195                 200                 205

Arg Pro His Phe Gly Val Glu Leu Pro Cys Thr Ser Tyr Gln Leu Thr
    210                 215                 220

Thr Ala Pro Thr Asp Glu Glu Ile Asp Met His Thr Pro Pro Asp Ile
225                 230                 235                 240

Pro Asp Arg Thr Leu Leu Ser Gln Thr Ala Gly Asn Val Lys Ile Thr
                245                 250                 255

Ala Gly Gly Arg Thr Ile Arg Tyr Asn Cys Thr Cys Gly Arg Asp Asn
            260                 265                 270

Val Gly Thr Thr Ser Thr Asp Lys Thr Ile Asn Thr Cys Lys Ile Asp
        275                 280                 285

Gln Cys His Ala Ala Val Thr Ser His Asp Lys Trp Gln Phe Thr Ser
    290                 295                 300

Pro Phe Val Pro Arg Ala Asp Gln Thr Ala Arg Arg Gly Lys Val His
305                 310                 315                 320

Val Pro Phe Pro Leu Thr Asn Val Thr Cys Arg Val Pro Leu Ala Arg
                325                 330                 335

Ala Pro Asp Val Thr Tyr Gly Lys Lys Glu Val Thr Leu Arg Leu His
            340                 345                 350

Pro Asp His Pro Thr Leu Phe Ser Tyr Arg Ser Leu Gly Ala Glu Pro
        355                 360                 365

His Pro Tyr Glu Glu Trp Val Asp Lys Phe Ser Glu Arg Ile Ile Pro
    370                 375                 380
```

```
Val Thr Glu Glu Gly Ile Glu Tyr Gln Trp Gly Asn Asn Pro Pro Val
385                 390                 395                 400

Arg Leu Trp Ala Gln Leu Thr Thr Glu Gly Lys Pro His Gly Trp Pro
                405                 410                 415

His Glu Ile Ile Gln Tyr Tyr Gly Leu Tyr Pro Ala Ala Thr Ile
            420                 425                 430

Ala Ala Val Ser Gly Ala Ser Leu Met Ala Leu Thr Leu Ala Ala
            435                 440                 445

Thr Cys Cys Met Leu Ala Thr Ala Arg Arg Lys Cys Leu Thr Pro Tyr
        450                 455                 460

Ala Leu Thr Pro Gly Ala Val Val Pro Leu Thr Leu Gly Leu Leu Cys
465                 470                 475                 480

Cys Ala Pro Arg Ala Asn Ala Ala Ser Phe Ala Glu Thr Met Ala Tyr
                485                 490                 495

Leu Trp Asp Glu Asn Lys Thr Leu Phe Trp Met Glu Phe Ala Ala Pro
            500                 505                 510

Ala Ala Ala Leu Ala Leu Leu Ala Cys Cys Ile Lys Ser Leu Ile Cys
            515                 520                 525

Cys Cys Lys Pro Phe Ser Phe Leu Val Leu Leu Ser Leu Gly Ala Ser
        530                 535                 540

Ala Lys Ala Tyr Glu His Thr Ala Thr Ile Pro Asn Val Val Gly Phe
545                 550                 555                 560

Pro Tyr Lys Ala His Ile Glu Arg Asn Gly Phe Ser Pro Met Thr Leu
                565                 570                 575

Gln Leu Glu Val Val Glu Thr Ser Leu Glu Pro Thr Leu Asn Leu Glu
            580                 585                 590

Tyr Ile Thr Cys Glu Tyr Lys Thr Val Val Pro Ser Pro Phe Ile Lys
            595                 600                 605

Cys Cys Gly Thr Ser Glu Cys Ser Ser Lys Glu Gln Pro Asp Tyr Gln
        610                 615                 620

Cys Lys Val Tyr Thr Gly Val Tyr Pro Phe Met Trp Gly Gly Ala Tyr
625                 630                 635                 640

Cys Phe Cys Asp Ser Glu Asn Thr Gln Leu Ser Glu Ala Tyr Val Asp
                645                 650                 655

Arg Ser Asp Val Cys Lys His Asp His Ala Ser Ala Tyr Lys Ala His
                660                 665                 670

Thr Ala Ser Leu Lys Ala Thr Ile Arg Ile Ser Tyr Gly Thr Ile Asn
            675                 680                 685

Gln Thr Thr Glu Ala Phe Val Asn Gly Glu His Ala Val Asn Val Gly
        690                 695                 700

Gly Ser Lys Phe Ile Phe Gly Pro Ile Ser Thr Ala Trp Ser Pro Phe
705                 710                 715                 720

Asp Asn Lys Ile Val Val Tyr Lys Asp Val Tyr Asn Gln Asp Phe
                725                 730                 735

Pro Pro Tyr Gly Ser Gly Gln Pro Gly Arg Phe Gly Asp Ile Gln Ser
                740                 745                 750

Arg Thr Val Glu Ser Lys Asp Leu Tyr Ala Asn Thr Ala Leu Lys Leu
            755                 760                 765

Ser Arg Pro Ser Pro Gly Val Val His Val Pro Tyr Thr Gln Thr Pro
        770                 775                 780

Ser Gly Phe Lys Tyr Trp Leu Lys Glu Lys Gly Ser Ser Leu Asn Thr
785                 790                 795                 800

Lys Ala Pro Phe Gly Cys Lys Ile Lys Thr Asn Pro Val Arg Ala Met
```

```
              805                 810                 815
Asp Cys Ala Val Gly Ser Ile Pro Val Ser Met Asp Ile Pro Asp Ser
                820                 825                 830
Ala Phe Thr Arg Val Val Asp Ala Pro Ala Val Thr Asp Leu Ser Cys
                835                 840                 845
Gln Val Val Cys Thr His Ser Ser Asp Phe Gly Gly Val Ala Thr
        850                 855                 860
Leu Ser Tyr Lys Thr Asp Lys Pro Gly Lys Cys Ala Val His Ser His
865                 870                 875                 880
Ser Asn Val Ala Thr Leu Gln Glu Ala Thr Val Asp Val Lys Glu Asp
                885                 890                 895
Gly Lys Val Thr Val His Phe Ser Thr Ala Ser Ala Ser Pro Ala Phe
                900                 905                 910
Lys Val Ser Val Cys Asp Ala Lys Thr Thr Cys Thr Ala Ala Cys Glu
                915                 920                 925
Pro Pro Lys Asp His Ile Val Pro Tyr Gly Ala Ser His Asn Asn Gln
        930                 935                 940
Val Phe Pro Asp Met Ser Gly Thr Ala Met Thr Trp Val Gln Arg Leu
945                 950                 955                 960
Ala Ser Gly Leu Gly Gly Leu Ala Leu Ile Ala Val Val Val Leu Val
                965                 970                 975
Leu Val Thr Cys Ile Thr Met Arg Arg
                980                 985

<210> SEQ ID NO 3
<211> LENGTH: 2224
<212> TYPE: DNA
<213> ORGANISM: Ebola virus

<400> SEQUENCE: 3
caacaacaca atgggcgtta caggaatatt gcagttacct cgtgatcgat tcaagaggac      60
atcattcttt ctttgggtaa ttatcctttt ccaaagaaca ttttccatcc cacttggagt     120
catccacaat agcacattac aggttagtga tgtcgacaaa ctagtttgtc gtgacaaact     180
gtcatccaca aatcaattga gatcagttgg actgaatctc gaagggaatg gagtggcaac     240
tgacgtgcca tctgcaacta aaagatgggc cttcaggtcc ggtgtcccac caaaggtggt     300
caattatgaa gctggtgaat gggctgaaaa ctgctacaat cttgaaatca aaaaacctga     360
cgggagtgag tgtctaccag cagcgccaga cgggattcgg gcttcccccc ggtgccggta     420
tgtgcacaaa gtatcaggaa cgggaccgtg tgccggagac tttgccttcc ataaagaggg     480
tgctttcttc ctgtatgatc gacttgcttc cacagttatc taccgaggaa cgactttcgc     540
tgaaggtgtc gttgcatttc tgatactgcc ccaagctaag aaggacttct tcagctcaca     600
ccccttgaga gagccggtca atgcaacgga ggacccgtct agtggctact attctaccac     660
aattagatat caggctaccg ttttggaac caatgagaca gagtacttgt tcgaggttga     720
caatttgacc tacgtccaac ttgaatcaag attcacacca cagtttctgc tccagctgaa     780
tgagacaata tatacaagtg ggaaaaggag caataccacg ggaaaactaa tttggaaggt     840
caaccccgaa attgatacaa catcggggga gtgggccttc tgggaaacta aaaaaaacct     900
cactagaaaa attcgcagtg aagagttgtc tttcacagtt gtatcaaacg gagccaaaaa     960
catcagtggt cagagtccgg cgcgaacttc tccgacccca gggaccaaca caacaactga    1020
agaccacaaa atcatggctt cagaaaattc ctctgcaatg gttcaagtgc acagtcaagg    1080
```

```
aagggaagct gcagtgtcgc atctaacaac ccttgccaca atctccacga gtccccaatc   1140
cctcacaacc aaaccaggtc cggacaacag cacccataat acaccgtgt ataaacttga    1200 catctctgag gcaactcaag ttgaacaaca tcaccgcaga acagacaacg acagcacagc   1260
ctccgacact ccctctgcca cgaccgcagc cggaccccca aaagcagaga acaccaacac   1320
gagcaagagc actgacttcc tggaccccgc caccacaaca agtccccaaa accacagcga   1380
gaccgctggc aacaacaaca ctcatcacca agataccgga gaagagagtg ccagcagcgg   1440
gaagctaggc ttaattacca atactattgc tggagtcgca ggactgatca caggcgggag   1500
aagaactcga agagaagcaa ttgtcaatgc tcaacccaaa tgcaacccta atttacatta   1560
ctggactact caggatgaag gtgctgcaat cggactggcc tggataccat atttcgggcc   1620
agcagccgag ggaatttaca tagagggggct aatgcacaat caagatggtt taatctgtgg   1680
gttgagacag ctggccaacg agacgactca agctcttcaa ctgttcctga gaccacaac    1740 tgagctacgc acctttcaa tcctcaaccg taaggcaatt gatttcttgc tgcagcgatg    1800
gggcggcaca tgccacattc tgggaccgga ctgctgtatc gaaccacatg attggaccaa   1860
gaacataaca gacaaaattg atcagattat tcatgatttt gttgataaaa cccttccgga   1920 ccaggggggac aatgacaatt ggtggacagg atggagacaa tggataccgg caggtattgg   1980
agttacaggc gttataattg cagttatcgc tttattctgt atatgcaaat ttgtcttta    2040 gttttttcttc agattgcttc atggaaaagc tcagcctcaa atcaatgaaa ccaggattta   2100
attatatgga ttacttgaat ctaagattac ttgacaaatg ataatataat acactggagc   2160
tttaaacata gccaatgtga ttctaactcc tttaaactca cagttaatca taaacaaggt   2220
ttga                                                                 2224
```

<210> SEQ ID NO 4
<211> LENGTH: 676
<212> TYPE: PRT
<213> ORGANISM: Ebola virus

<400> SEQUENCE: 4

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
```

```
                         165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
            195                 200                 205
Pro Ser Ser Gly Tyr Tyr Ser Thr Thr Ile Arg Tyr Gln Ala Thr Gly
        210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
            260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
        290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
        370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
        435                 440                 445
Thr Thr Ser Pro Gln Asn His Ser Glu Thr Ala Gly Asn Asn Asn Thr
        450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
        515                 520                 525
Leu Ala Trp Ile Pro Tyr Phe Gly Pro Ala Ala Glu Gly Ile Tyr Ile
        530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Phe Ser Ile Leu Asn Arg Lys Ala Ile Asp Phe
            580                 585                 590
```

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 5
<211> LENGTH: 2103
<212> TYPE: DNA
<213> ORGANISM: Marburg virus

<400> SEQUENCE: 5

| | |
|---|---|
| taccctaaca tgaagaccac atgtttcctt atcagtctta tcttaattca agggacaaaa | 60 |
| aatctcccca tttagagat agctagtaat aatcaacccc aaaatgtgga ttcggtatgc | 120 |
| tccggaactc tccagaagac agaagacgtc catctgatgg gattcacact gagtgggcaa | 180 |
| aaagttgctg attccccttt ggaggcatcc aagcgatggg cttcaggac aggtgtacct | 240 |
| cccaagaatg ttgagtacac agaggggag gaagccaaaa catgctacaa tataagtgta | 300 |
| acggatccct ctggaaaatc cttgctgtta gatcctccta ccaacatccg tgactatcct | 360 |
| aaatgcaaaa ctatccatca tattcaaggt caaaaccctc atgcacaggg gatcgccctt | 420 |
| catttatggg gagcattttt tctgtatgat cgcattgcct ccacaacaat gtaccgaggc | 480 |
| aaagtcttca ctgaagggaa catagcagct atgattgtca ataagacagt gcacaaaatg | 540 |
| attttctcgc ggcaaggaca agggtaccgt catatgaatc tgacttctac taataaatat | 600 |
| tggacaagta gtaacggaac gcaaacgaat gacactggat gtttcggcgc tcttcaagaa | 660 |
| tacaattcta caaagaacca acatgtgct ccgtccaaaa tacctccacc actgcccaca | 720 |
| gcccgtccgg agatcaaact cacaagcacc ccaactgatg ccaccaaact caataccacg | 780 |
| gacccaagca gtgatgatga ggacctcgca acatccggct cagggtccgg agaacgagaa | 840 |
| ccccacacaa cttctgatgc ggtcaccaag caagggcttt catcaacaat gccaccact | 900 |
| ccctcaccac aaccaagcac gccacagcaa ggaggaaaca acacaaacca ttcccaagat | 960 |
| gctgtgactg aactagacaa aaataacaca actgcacaac cgtccatgcc ccctcataac | 1020 |
| actaccacaa tctctactaa caacacctcc aaacacaact tcagcactct ctctgcacca | 1080 |
| ttacaaaaca ccaccaatga caacacacag agcacaatca ctgaaaatga gcaaaccagt | 1140 |
| gcccctcga taacaaccct gcctccaacg ggaaatccca ccacagcaaa gagcaccagc | 1200 |
| agcaaaaaag ccccgccac aacggcacca aacacgacaa atgagcattt caccagtcct | 1260 |
| ccccccaccc ccagctcgac tgcacaacat cttgtatatt tcagaagaaa gcgaagtatc | 1320 |
| ctctggaggg aaggcgacat gttccctttt ctggatgggt taataaatgc tccaattgat | 1380 |
| tttgacccag ttccaaatac aaaaacaatc tttgatgaat cctctagttc tggtgcctcg | 1440 |
| gctgaggaag atcaacatgc ctccccccaat attagtttaa cttatctta ttttcctaat | 1500 |
| ataaatgaga acactgccta ctctggagaa atgagaatg attgtgatgc agagttaaga | 1560 |

-continued

```
atttggagcg ttcaggagga tgacctggcc gcagggctca gttggatacc gttttttggc    1620
cctggaattg aaggactttta cactgctgtt ttaattaaaa atcaaaacaa tttggtctgc    1680
aggttgaggc gtctagccaa tcaaactgcc aaatccttgg aactcttatt gagagtcaca    1740
actgaggaaa gaacattctc cttaatcaat agacatgcta ttgactttct actcacaaga    1800
tggggaggaa catgcaaagt gcttggacct gattgttgca tcgggataga agacttgtcc    1860
aaaaatattt cagagcaaat tgaccaaatt aaaaaggacg aacaaaaaga ggggactggt    1920
tggggtctgg gtggtaaatg gtggacatcc gactggggtg ttcttactaa cttgggcatt    1980
ttgctactat tatccatagc tgtcttgatt gctctatcct gtatttgtcg tatctttact    2040
aaatatatcg gataacgtta aatgtgtaat gattaggact ttaggacaat tgctactgag    2100
ccc                                                                   2103
```

<210> SEQ ID NO 6
<211> LENGTH: 681
<212> TYPE: PRT
<213> ORGANISM: Marburg virus

<400> SEQUENCE: 6

```
Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Ala Leu Gln Glu Tyr Asn Ser Thr Lys Asn Gln
    210                 215                 220

Thr Cys Ala Pro Ser Lys Ile Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270
```

```
Ser Gly Glu Arg Glu Pro His Thr Thr Ser Asp Ala Val Thr Lys Gln
    275                 280                 285

Gly Leu Ser Ser Thr Met Pro Pro Thr Pro Ser Pro Gln Pro Ser Thr
290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
                340                 345                 350

Thr Leu Ser Ala Pro Leu Gln Asn Thr Thr Asn Asp Asn Thr Gln Ser
                355                 360                 365

Thr Ile Thr Glu Asn Glu Gln Thr Ser Ala Pro Ser Ile Thr Thr Leu
                370                 375                 380

Pro Pro Thr Gly Asn Pro Thr Thr Ala Lys Ser Thr Ser Ser Lys Lys
385                 390                 395                 400

Gly Pro Ala Thr Thr Ala Pro Asn Thr Thr Asn Glu His Phe Thr Ser
                405                 410                 415

Pro Pro Pro Thr Pro Ser Ser Thr Ala Gln His Leu Val Tyr Phe Arg
                420                 425                 430

Arg Lys Arg Ser Ile Leu Trp Arg Glu Gly Asp Met Phe Pro Phe Leu
            435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
                500                 505                 510

Asp Ala Glu Leu Arg Ile Trp Ser Val Gln Glu Asp Leu Ala Ala
                515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
                565                 570                 575

Thr Thr Glu Glu Arg Thr Phe Ser Leu Ile Asn Arg His Ala Ile Asp
                580                 585                 590

Phe Leu Leu Thr Arg Trp Gly Gly Thr Cys Lys Val Leu Gly Pro Asp
            595                 600                 605

Cys Cys Ile Gly Ile Glu Asp Leu Ser Lys Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
                660                 665                 670

Cys Arg Ile Phe Thr Lys Tyr Ile Gly
    675                 680
```

```
-continued

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
cgggatccac catgtctgcc gcgct                                              25

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
cgctctagat taccgacgca ttgttatg                                           28
```

PSEUDOTYPED RETROVIRUSES AND STABLE CELL LINES FOR THEIR PRODUCTION

REFERENCE TO RELATED APPLICATIONS

This present application is a National Stage entry of International Application No. PCT/US99/17702, filed Aug. 4, 1999, which claims the benefit of U.S. Patent Provisional Patent Application Ser. No. 60/095,242, filed Aug. 4, 1998, and U.S. Provisional Patent Application Ser. No. 60/112, 405, filed Dec. 15, 1998, which are both hereby incorporated by reference in their entirety.

BACKGROUND OF THE INVENTION

The present invention relates generally to cells that produce pseudotyped retroviruses having broad host range. Specifically, the invention relates to cells that produce retroviruses pseudotyped with glycoproteins derived from either filoviruses or viruses having at least two different viral glycoproteins disposed in their lipid bilayer. The invention further relates to methods of producing such cells, the pseudotyped retroviruses produced, methods of making and using the pseudotyped retroviruses and kits for producing the pseudotyped retroviruses.

Retroviruses are ribonucleic acid (RNA) viruses that include an RNA genome enclosed within a viral capsid wherein the capsid is surrounded by an envelope, or lipid bilayer. Glycoproteins present in the lipid bilayer (envelope glycoproteins) interact with receptors on the surface of various host cells and allow the retroviruses to enter the host cell. Once in the cell, the retroviruses reverse transcribe the RNA of the viral genome into a double-stranded DNA (a proviral intermediate), and incorporate the deoxyribonucleic acid (DNA) into the cellular genome as a provirus. Gene products from the integrated foreign DNA may then be produced so that progeny viral particles may be assembled. As retroviruses can be modified to carry exogenous nucleotide sequences of interest, such recombinant retroviruses have a variety of uses. For example, such recombinant retroviruses are important in introducing desired exogenous sequences into a cell, so that relatively high levels of the protein encoded by the sequences may be produced. However, use of such recombinant retroviruses has several drawbacks.

For example, retroviruses do not have a broad host range. Efforts at increasing the host range of retroviruses have included substituting the envelope glycoproteins of the virus with that of a different virus, thus forming a pseudotyped retrovirus. The pseudotyped retrovirus advantageously has the host range of the different virus. However, some retroviruses have been pseudotyped with viral glycoproteins that are toxic to cells, so the cells can only produce the virus for a limited time. Furthermore, in many cases, the pseudotyped retroviruses can not be stably produced and may not be produced at a high titer.

There is therefore a need for pseudotyped retroviruses of broad host range, and cell lines capable of producing such pseudotyped retroviruses. The present invention addresses this need.

SUMMARY OF THE INVENTION

It has been discovered that cells may be constructed to produce inventive retroviruses pseudotyped with viral glycoproteins, wherein the retroviruses have a broad host range.

Accordingly, one aspect of the invention provides eukaryotic cells that include a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein. In one preferred embodiment, the fourth nucleotide sequence encodes at least two different viral glycoproteins, preferably togaviral glycoproteins, such as, for example, alphaviral glycoproteins. In alternative embodiments, the fourth nucleotide sequence encodes a filoviral glycoprotein, such as, for example, a Marburg virus or Ebola virus glycoprotein. In a preferred form of the invention, the cells stably produce inventive pseudotyped retroviruses.

A second aspect of the invention provides methods of forming the above-described eukaryotic cells. The method includes transfecting a eukaryotic cell with a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein. In one preferred embodiment, the fourth nucleotide sequence encodes at least two different viral glycoproteins, preferably togaviral glycoproteins. In alternative embodiments, the fourth nucleotide sequence encodes a filoviral glycoprotein, such as a Marburg virus glycoprotein. In preferred forms of the invention, the first, second, third and fourth nucleotide sequences are chromosomally-integrated, wherein the cell stably produces inventive pseudotyped retroviruses.

A third aspect of the invention provides inventive pseudotyped retroviruses, including a retroviral capsid, a lipid bilayer surrounding the retroviral capsid and at least one viral glycoprotein disposed in the lipid bilayer. In inventive pseudotyped retroviruses, at least two different viral glycoproteins are disposed in the lipid bilayer, and in preferred embodiments, the viral glycoproteins are togaviral glycoproteins. In an alternative embodiment, the viral glycoprotein is a filoviral glycoprotein, preferably a Marburg virus glycoprotein.

In yet a fourth aspect of the present invention, methods of introducing nucleotide sequences into a cell are provided, and include transducing a cell permissive for viral entry with a pseudotyped retrovirus having a retroviral capsid, a lipid bilayer surrounding the retroviral capsid, at least one viral glycoprotein disposed in the lipid bilayer and a desired ribonucleotide sequence. In one preferred form of the invention, the cells are permissive for entry of a virus having at least two different viral glycoproteins in its lipid bilayer, such as a togavirus wherein the viral glycoproteins are togaviral glycoproteins. In alternative embodiments, the viral glycoprotein is a filoviral glycoprotein, preferably a Marburg virus glycoprotein.

A fifth aspect of the invention provides methods of screening agents effective in blocking viral entry into a cell. In one mode of practicing the invention, the method includes treating a pseudotyped retrovirus with the agent, treating a cell permissive for viral entry with the treated pseudotyped retrovirus and identifying eukaryotic cells having the desired marker. In one embodiment, the pseudotyped retrovirus has a retroviral capsid, a lipid bilayer surrounding the capsid, at least two different viral glycoproteins disposed in its lipid bilayer, such as togaviral glycoproteins wherein the cell is permissive for togaviral entry, and a nucleotide sequence encoding a desired marker. In alternative embodiments, a method is provided for screening agents effective in blocking filoviral entry, preferably Marburg virus entry, into a cell.

Pseudotyped retroviruses having Marburg virus glycoprotein disposed in their lipid bilayer are preferred as are cells permissive for Marburg virus entry.

In yet another embodiment of a method of screening agents effective in blocking viral entry into a cell, the method includes treating a cell permissive for entry of a virus having at least two different viral glycoproteins disposed in its lipid bilayer with said agent, contacting the treated cell with a pseudotyped retrovirus having a retroviral capsid, a lipid bilayer that surrounds the retroviral capsid, at least two different viral glycoproteins disposed in its lipid bilayer, such as togaviral glycoproteins wherein the cell is permissive for togaviral entry, and a nucleotide sequence encoding a desired marker, and identifying cells having the marker. In alternative embodiments, a method is provided for screening agents effective in blocking filoviral entry, preferably Marburg virus entry, into a cell. Pseudotyped retroviruses having Marburg virus glycoprotein disposed in their lipid bilayer are preferred as are cells permissive for Marburg virus entry.

In a sixth aspect of the present invention, kits for forming inventive pseudotyped retroviruses are provided. The kits include a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein. In one embodiment, the fourth nucleotide sequence encodes at least two viral glycoproteins, such as togaviral glycoproteins. In alternative embodiments, the fourth nucleotide sequence encodes a Marburg virus glycoprotein.

One object of the invention is to provide a eukaryotic cell including a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein, such as a Marburg virus glycoprotein, preferably at least two viral glycoproteins, such as togaviral glycoproteins and especially alphaviral glycoproteins.

Another object is to provide a eukaryotic cell that includes a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein, such as a Marburg virus glycoprotein, preferably at least two viral glycoproteins, such as togaviral glycoproteins and especially alphaviral glycoproteins, wherein the cell stably produces the inventive pseudotyped retroviruses.

Another object is to provide a method of making the inventive cells described above, as well as the pseudotyped retroviruses so produced.

Other objects are to provide a method of screening agents effective in blocking either filoviral entry into a cell or entry of viruses having more than one viral glycoprotein in their lipid bilayer, such as togaviruses, and methods of introducing desired nucleotide sequences into a cell.

Yet other objects of the invention are to provide kits for forming inventive pseudotyped retroviruses.

These and other objects and advantages of the present invention will be apparent from the descriptions herein.

BRIEF DESCRIPTION OF THE FIGURES

FIG. 3 depicts graphs showing the effects of lysosomotropic agents on transduction of the indicated retroviruses. Left panel, A.

DESCRIPTION OF THE PREFERRED EMBODIMENTS

Figure 1:
FIG. 1 shows a Western blot of proteins derived from lysates of stable cell line SafeRRnlslacZ, or precursor gpnlslacz cells, as further described in Example 4.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to eukaryotic cells that stably produce pseudotyped retroviruses and methods for their production, pseudotyped retroviruses, methods of introducing nucleotide sequences into a target cell, methods of screening agents effective in blocking viral entry into cells and kits for forming inventive pseudotyped retroviruses.

It has been discovered that eukaryotic cells may be constructed that either transiently or stably produce pseudotyped retroviruses having at least two different viral glycoproteins disposed in their lipid bilayer, such as togaviral glycoproteins. It has further been discovered that eukaryotic cells may be constructed that stably produce pseudotyped retroviruses having filoviral glycoproteins disposed in their lipid bilayer. The pseudotyped retroviruses of the present invention are advantageous in transducing cells of interest, are not toxic to the cells, have a broad host range and do not allow for pseudotransduction (i.e., introduction of proteins and/or genetic material without stable transmission of genetic material). Moreover, the present disclosure is the first report of a pseudotyped retrovirus having two different viral glycoproteins, with different membrane spanning domains, disposed in its lipid bilayer.

Accordingly, one aspect of the invention provides inventive eukaryotic cells having nucleotide sequences encoding retroviral Gag polypeptide, retroviral Pro polypeptide, retroviral Pol polypeptide and at least one viral glycoprotein, such as a filoviral glycoprotein, or at least two viral glycoproteins, such as togaviral glycoproteins. In a preferred embodiment, nucleotide sequences encoding the polypeptides described are chromosomally-integrated and thus stably produce inventive pseudotyped retroviruses. A second aspect of the invention provides methods of forming cells that produce inventive pseudotyped retroviruses. A third aspect of the invention provides the inventive pseudotyped retroviruses, preferably those that include at least two different viral glycoproteins disposed in their lipid bilayer, including togaviral glycoproteins, and further preferably those that include a desired nucleotide sequence in their genome. Other aspects of the invention provide inventive methods of introducing a nucleotide sequence into a desired cell and methods of screening agents effective in blocking viral entry into a target cell, preferably blocking entry of a Marburg virus, or a virus having more than one viral glycoprotein in its lipid bilayer such as a togavirus, wherein all of the methods utilize the inventive pseudotyped retroviruses and cells described above, and kits for producing inventive pseudotyped retroviruses.

As discussed above, one aspect of the invention provides eukaryotic cells, forming inventive eukaryotic cell lines, having nucleotide sequences encoding retroviral Gag polypeptide, retroviral Pro polypeptide, retroviral Pol polypeptide and at least one viral glycoprotein, such as a filoviral glycoprotein, or at least two different viral glycoproteins, typically from the same virus, such as togaviral glycoproteins. The term "eukaryotic cell line" as used herein is intended to refer to eukaryotic cells that are grown in vitro. The term "nucleotide sequence", as used herein, is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

In forming a cell that produces an inventive pseudotyped retrovirus, a wide variety of cells may be selected. Eukaryotic cells are preferred, whereas mammalian cells are more preferred, and include human, simian canine, feline, equine and rodent cells. Human cells are most preferred. It is further preferred that the cell be able to reproduce indefinitely, and is therefore immortal. Examples of cells that may be advantageously used in the present invention include NIH 3T3 cells, COS cells, Madin-Darby canine kidney cells and human embryonic 293T cells. However, highly transfectable cells, such as human embryonic kidney 293T cells, are preferred. By "highly transfectable" it is meant that at least about 50%, more preferably at least about 70% and most preferably at least about 80% of the cells can express the genes of the introduced DNA.

The retroviral gag, pro and pol nucleotide sequences, and other retroviral nucleotide sequences for forming the specified pseudotyped retroviruses, may be obtained from a wide variety of genera in the family Retroviridae, including, for example, Oncoviruses, including Oncovirus A, B, C and D, lentiviruses and spumavirus F. Such sequences are preferably obtained from the Moloney murine leukemia virus (MMLV; in the genus Oncovirus C). Such sequences are well known in the art. For example, nucleotide sequences encoding MMLV gag, pro and pol may be found in Van Bereven et al. *Cell* (1981)27:97–108. Most preferably, such sequences are obtained from lentiviruses. Unlike most retroviruses, lentiviruses have the capacity to integrate the genetic material they carry into the chromosomes of non-dividing cells as well as dividing cells. Therefore, lentiviral nucleotide sequences encoding proteins that allow for chromosomal integration of virally transported nucleic acid in non-dividing cells are advantageously employed, as the host range of the peudotyped retroviruses will be broadened.

The above-described retroviruses are readily publicly available from the American Type Culture Collection (ATCC) and the desired nucleotide sequences may be obtained from these retroviruses by methods known to the skilled artisan. For example, the nucleotide sequences may be obtained by recombinant DNA technology. Briefly, viral DNA libraries may be constructed and the nucleotide sequences may be obtained by standard nucleic acid hybridization or polymerase chain reaction (PCR) procedures, using appropriate probes or primers. Alternatively, supernatant medium from cells infected with the respective virus can be isolated and the desired retroviral nucleotide sequences may be amplified by PCR. Such vectors may also be constructed by other methods known to the art.

It is preferred that the gag, pro and pol nucleotide sequences are contiguous to each other as found in native retroviral genomes, such as in the order 5'-gag-pro-pol-3'. It is further preferred that these retroviral nucleotide sequences are chromosomally-integrated into the cellular genome. Furthermore, the gag-pro-pol nucleotide sequences are operably linked at the 5' end of the gag nucleotide sequence to a promoter sequence, so that transcription of the sequences may be achieved.

A nucleic acid sequence is "operably linked" to another nucleic acid sequence, such as a promoter sequence, when it is placed in a specific functional relationship with the other nucleic acid sequence. The functional relationship between a promoter and a desired nucleic acid typically involves the nucleic acid and the promoter sequences being contiguous such that transcription of the nucleic acid sequence will be facilitated. Two nucleic acid sequences are further said to be operably linked if the nature of the linkage between the two sequences does not (1) result in the introduction of a frame-shift-mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid coding sequence.

A wide variety of promoters are known in the art, including cell-specific promoters, inducible promoters, and constitutive promoters. The promoters may further be selected such that they require activation by activating elements known in the art, so that production of the protein encoded by the specified nucleic acid sequence may be regulated as desired. It is well within the purview of a person skilled in the art to select and use an appropriate promoter in accordance with the present invention. For example, the promoters that may be advantageously present in the cell, 5' to the gag-pro-pol sequences, include rat actin promoter and the MMLV promoter. Furthermore, the cytomegalovirus promoter has been found to be an excellent promoter in the inventive system.

Other regulatory elements, such as enhancer sequences, which cooperate with the promoter and transcriptional start site to achieve transcription of the nucleic acid insert coding sequence, may also be present in the cell 5' to the nucleotide sequences that encode retroviral proteins. By "enhancer" is meant nucleotide sequence elements which can stimulate promoter activity in a cell, such as a bacterial or eukaryotic host cell.

A wide variety of viral glycoproteins may be advantageously present in the inventive cells of the present invention, especially viral glycoproteins necessary for attachment of the virus to a target cell and penetration of the virus into the cytoplasm of the cell, as well as viral glycoproteins necessary for maturation of the glycoproteins necessary for attachment and penetration of the virus. For example, the cells described above may include nucleotide sequences encoding at least two different viral glycoproteins. Examples of such viruses include viruses in the families Togaviridae (e.g., in the genus Alphavirus or Rubivirus), Flaviviridae (e.g., Flavivirus, Pestivirus and Hepatitic C), Paramyxoviridae (e.g., Morbillivirus), and Bunyaviridae (e.g., Hantavirus). Such nucleotide sequences are well known to the art. In one embodiment, the cells may include, instead of the viral nucleotide sequences encoding at least two different viral glycoproteins, nucleotide sequences encoding filoviral glycoproteins. Examples of such viruses include Ebola virus (including Ebola Zaire, Ebola Reston and Ebola Sudan sequences which are chromosomally-integrated), and Marburg virus. These nucleotide sequences may be obtained by methods known in the art as recited in example 2. For example, nucleotide sequences encoding particular glycoproteins may be isolated and cloned into plasmids by standard techniques, and the nucleotide sequence may then be amplified by PCR using the appropriate primers.

In one form of the present invention, the cells include nucleotide sequences encoding glycoproteins from an alphavirus. In a most preferred embodiment, the cells include nucleotide sequences encoding glycoproteins from the viral species Ross River (depicted in SEQ ID NO:1 and SEQ ID NO:2). The viral transmembrane glycoprotein complex that is responsible for the binding of the alphavirus to the surface of a susceptible cell and for the fusion of the viral and cellular membranes that occurs during the process of viral entry includes a trimer of a heterodimer of two transmembrane proteins, which are denoted $E_1$ and $E_2$ and which are encoded by an $E_3$-$E_2$-6K-$E_1$ glycoprotein coding region ($E_3$ and 6K refer to viral proteins involved in maturation of $E_1$ and $E_2$ as known in the art) on the alphaviral genome. The $E_2$-$E_1$ coding region includes an $E_3$ glycoprotein coding region as well as the 6K protein coding region. Such nucleotide sequences may be obtained by methods known to the skilled artisan as discussed for the gag, pro and pol nucleotide sequences above. For example, the $E_2$-$E_1$ coding region may be obtained as discussed in Kuhn et al. (1991) Virology 182:430–441. The $E_2$-$E_1$ glycoprotein coding region is also operably linked to a promoter sequences, such as described above, at its 5' end.

The eukaryotic cells described above, that include nucleotide sequences encoding togaviral glycoproteins, advantageously produce retroviruses pseudotyped with togaviral glycoproteins at a titer of at least about $1\times10^3$ transforming units (TU)/ml of cell culture supernatant medium. The cells more preferably produce such retroviruses at a titer of at least about $1\times10^5$ TU/ml of supernatant and most preferably at a titer of at least about $1\times10^6$ TU/ml of supernatant.

It is expected that other viruses not specifically mentioned herein having at least two different glycoproteins of similar structure to the glycoproteins in the viral families denoted above may be advantageously used in the present invention.

In another embodiment, the cells include nucleotide sequences encoding glycoproteins from a filovirus. Such filoviruses also exhibit a broad host range. A wide variety of nucleotide sequences that encode filoviral glycoproteins may be used to produce the inventive cells of the present invention. For example, nucleotide sequences encoding glycoproteins from the Marburg and Ebola virus (in the family Filoviridae and, including, for example, Ebola-Zaire and Ebola-Reston) may be introduced into the cells described above to produce a pseudotyped retrovirus. SEQ ID NO:3 shows the Ebola Zaire glycoprotein-encoding sequence and SEQ ID NO:5 shows the Marburg virus glycoprotein-encoding sequence. The nucleotide sequences encoding the filoviral glycoproteins may be obtained as described in Sanchez et al. (1993) *Virus Res.* 29(3):215–240 and Will et al., (1993) *J. Virol.* 67:1203–1210. Moreover, such sequences may be obtained by other methods known to those skilled in the art, as described above for the togaviruses.

Eukaryotic cells described above that include the filoviral nucleotide sequences advantageously produce retroviruses pseudotyped with a filoviral glycoprotein at a titer of at least about $4.5\times10^4$ TU/ml of supernatant. The cells more preferably produce such retroviruses at a titer of at least about $1\times10^6$ TU/ml of supernatant and most preferably at a titer of at least about $1\times10^7$ TU/ml of supernatant.

It is expected that other viruses not specifically mentioned above and having glycoproteins of similar structure to the filoviral glycoproteins may be advantageously used in the present invention.

The cells may transiently produce the retrovirus pseudotyped with at least two different viral glycoproteins, such as togaviral glycoproteins, or with a filoviral glycoprotein, but preferably stably produce such retroviruses. In one preferred form of the present invention, the nucleotide sequences encoding either the filoviral glycoproteins or encoding at least two different viral glycoproteins (such as togaviral glycoproteins) in the eukaryotic cells are chromosomally-integrated, so that the cell stably produces the pseudotyped retrovirus. By "stably produce", it is meant that the cells will produce pseudotyped retrovirus indefinitely (i.e., during the life span of the cell). Conversely, by transient production, it is meant that the cells will produce pseudotyped retrovirus for a period of at least about 24 hours, more preferably at least about 48 hours, and most preferably at least about 72 hours.

In a further preferred form of the present invention, the eukaryotic cells described above may include another nucleotide sequence that encodes a desired protein so that they may produce pseudotyped retroviruses having an RNA genome including such desired nucleotide sequences. The protein can be such that it provides a beneficial or therapeutic effect if introduced into an animal. For example, a gene may encode a protein that is needed by an animal, either because the protein is no longer produced, is produced in insufficient quantities to be effective in performing its function, or is mutated such that it either no longer functions or is only partially active for its intended function. The nucleotide sequence may be introduced into the cellular genome in a variety of ways known to the skilled artisan. For example, defective retroviruses (i.e., those which do not have the capability to produce all of the viral proteins necessary for production of a retrovirus having the ability to infect a cell and produce progeny viruses) may be constructed to include such a sequence in their RNA genome and can then transduce a cell. Alternatively, and as described above, plasmid vectors may be used to introduce the nucleotide sequence, preferably DNA, encoding the desired protein. In either case, the vector typically includes nucleotide sequences necessary for production of the pseudotyped retrovirus. For example, the RNA sequence in the viral genome is flanked on the 5' end by a splice acceptor site and a splice donor site followed by a sequence necessary for packing of the viral genome (such as a psi sequence) and a long terminal repeat (LTR), all as known in the art. The 3' end of the RNA sequence may be flanked on its 3' end with a polypurine tract followed by another LTR, further as known to the skilled artisan. The vectors may include other nucleotide sequences known to the art that are necessary for transduction.

In one preferred form, the desired protein may be one that allows entry of the virus into a cell to be detected. For example, a visually detectable component, or marker, such as one that emits visible wavelengths of light, or that may be reacted with a substrate to produce color of specified wavelengths. For example, such nucleotide sequences include the nucleotide sequence encoding the *Aequorea victoria* green fluorescent protein [GFP; nucleotide sequences listed in Prasher et al., (1992) *Gene* 111:229] and the LacZ gene (produces β-galactosidase), both of which are well known in the art and may be obtained commercially.

A second aspect of the invention provides methods of forming eukaryotic cells for producing pseudotyped retroviruses. The method includes introducing into the cells described above the nucleotide sequences described above, i.e., those encoding the retroviral Gag, Pro and Pol polypeptides, and those encoding either a filoviral glycoprotein or at least two different viral glycoproteins, such as togaviral glycoproteins, into the cell.

The nucleotide sequences may be introduced into the desired cell utilizing a variety of vectors known to the skilled artisan. For example, plasmid vectors, cosmid vectors, and other viral vectors, such as retroviral vectors, may be used. It is preferred that the nucleotide sequences encoding the Gag, Pro and Pol polypeptides are on a separate vector than the nucleotide sequences encoding the viral glycoproteins.

In one mode of practicing the invention, plasmid vectors are advantageously used to introduce, or transfect, the nucleotide sequences into the selected cell. A wide variety of plasmid vectors may be used, including pTRE, pCMV-Script and pcDNA3, although pcDNA3 is a preferred vector. The gag, pro and pol nucleotide sequences are preferably on the same plasmid, and, as discussed above, are preferably contiguous to each other. However, the skilled artisan is aware that other spatial configurations of the nucleotide sequences may be utilized when constructing the plasmids. The vector also preferably includes a promoter 5' to, or upstream from, the gag nucleotide sequence. The vectors may further include other regulatory elements, such as enhancer sequences, as discussed above.

The nucleotide sequences encoding the viral glycoproteins are preferably on a separate plasmid, or other vector, than the gag, pro and pol nucleotide sequences. The viral glycoprotein encoding sequences, such as the sequences encoding either the filoviral glycoproteins or those encoding at least two different viral glycoproteins (such as togaviral glycoproteins) are also preferably operably linked to a promoter sequence described above. It is also understood that the nucleotide sequences encoding at least two different viral glycoproteins may be arranged on a vector such that the nucleotide sequences encoding one of the glycoproteins are present on one vector and the sequences encoding the other glycoprotein are present on a different vector. It is preferred, however, that such sequences are on the same vector, and preferably contiguous to each other so they will be transcribed utilizing the same promoter. In one preferred form of the invention, the promoter sequence is a cytomegalovirus promoter sequence. Plasmids, or other vectors carrying the nucleotide sequences encoding the viral glycoproteins, may also include other regulatory elements, such as enhancers, as described above.

The vectors may be introduced into the cells in a variety of ways known to the skilled artisan, for example, discussed in *Current Protocols in Molecular Biology*, John Wiley and Sons, edited by Ausubel et al. (1988) and Maniatis, et al., *Molecular Cloning, A Laboratory Manual*, Cold Spring Harbor Laboratory (1989). For example, vectors may be transfected into a cell by a calcium phosphate precipitation method. Other methods for introduction of the vectors include, for example, electroporation and lipofection.

The nucleotide sequences may be introduced into the cells by a transient transfection procedure such that the proteins encoded by the respective sequences will be produced in a transient fashion as described above. By introducing the MMLV gene sequences and the $E_2$-$E_1$ coding region from the Ross River virus (RRV) described above into a cell, we have determined that the cell lines produce pseudotyped retrovirus for a period of about 48 hours. However, it is preferred that the sequences are stably introduced. That is, it is preferred the nucleotide sequences become integrated into chromosomes of the cells into which they are introduced. In this way, the cells will stably produce pseudotyped retrovirus for a longer period of time compared to the transient expression. As used herein, a "stable cell line" or "stable cell" is defined as one that has chromosomally-integrated the nucleotide sequences described above and can produce pseudotyped retrovirus indefinitely (i.e., for the life span of the cell).

Furthermore, in order to form such stable cells, it is necessary to use selectable markers to screen for cells which have chromosomally-integrated the introduced DNA. Accordingly, the plasmid vectors, or other vectors, into which the respective nucleotide sequences are cloned may include such selectable markers.

A wide variety of selectable markers may be used. Typical selectable markers allow growth of only those cells which have been transfected or transduced and thereby stably produce a desired protein. Examples of selectable markers that may be used include antibiotic resistance genes, including the neomycin gene, the hygromycin phosphotransferase gene and the bleomycin resistance gene which confer resistance to G418, hygromycin and zeocin, respectively. Other selectable markers include, for example, mutant mouse dihydrofolate reductase gene (confers resistance to methotrexate), and the bacterial gpt gene (selects for cells that can grow in a medium containing mycophenolic acid, xanthin and aminopterin). These selectable markers are discussed in *Retroviruses*, Cold Spring Harbor Laboratory Press, p. 444, edited by Coffin, J. M, Hughes, S. H. and Varmus, H. E. (1997).

In many cases, one may wish to quickly visually detect those cells which have taken up a vector and that produce a specified protein from the vector. Visually detectable components, or markers, include the *Aequorea victoria* green fluorescent protein as discussed above. When forming a cell that includes a visually detectable component, or marker, the nucleotide sequences encoding the marker may also be introduced into the cell as described above. For example, the nucleotide sequence encoding the green fluorescent protein may be placed in a recombinant MMLV genome or in a plasmid (to form plasmid MFG.S-GFP) by methods known to the art. For example, plasmid MFG.S-GFP may be formed by including in plasmid MFG [produced by methods known in the art and as exemplified by Ory et al., *PNAS USA*, 93:11400–11406 (1996)] the nucleotide sequence encoding the green fluorescent protein, surrounded by the nucleotide sequences described above, such as LTRs and the psi sequence. Cells that have taken up the vector and express the nucleotide sequences encoding a protein may be identified and separated from cells that do not express the sequences by a fluorescensce-activated cell sorting procedure as known in the art. A visually detectable marker may also be formed from reaction of β-galactosidase (produced by the LacZ gene) with a substrate, such as X-gal.

Moreover, when growing cells that produce inventive pseudotyped retroviruses, the cells should be grown to no more than about 50% confluency, more preferably no more than about 25% confluency, and the pH of the culture medium should be maintained at about 7 by the frequent changing of culture medium. These conditions are conducive for production of cells that stably produce the pseudotyped retroviruses and should be strictly followed.

In a third aspect of the present invention, pseudotyped retroviruses that include viral glycoproteins (as discussed above) disposed in their lipid bilayer are provided. In one embodiment, at least two different viral glycoproteins are present in the lipid bilayer, such as togaviral glycoproteins. In alternative embodiments the glycoprotein is a filoviral glycoprotein.

In one embodiment, such pseudotyped retroviruses include a core RNA genome that is surrounded by, or enclosed within, a viral capsid. The genome preferably includes a nucleotide sequence encoding a protein selected to be subsequently produced by a cell. The genome further includes other nucleotide sequences for formation of the pseudotyped retrovirus, such as 5' and 3' LTR sequences that are operably linked to the nucleotide sequence encoding the desired protein as described above. Reverse transcriptase and integrase are also enclosed within the capsid, which gives the retrovirus the ability to incorporate a gene encoding a desired protein into a genome of a cell after the retrovirus contacts, or is incubated with, the cell. For example, the pseudotyped retrovirus may be used to incorporate a gene encoding an enzyme in a host cell that is incapable of producing the enzyme, or produces a non-functional enzyme as discussed above. Other sequences known to the art that are useful for transducing genes may also be present in the RNA genome.

The pseudotyped retrovirus may include other proteins, in addition to integrase, that aid its stable integration into the chromosomes of a target cell. For example, with respect to a lentivirus, the pseudotyped retrovirus may include proteins such as vpr, vif and vpu.

In yet other preferred embodiments, the pseudotyped retrovirus may include a nucleotide sequence encoding a visually detectable component, or marker, such as *Aequorea victoria* green fluorescent protein as discussed above. Such a retrovirus may be advantageously used in a method of determining viral entry into a cell discussed above. Moreover, such a virus is advantageously used in the methods of the present invention to ensure that the pseudotyped retroviruses that are formed are replication incompetent (i.e., do not have all the sequences necessary in their viral genome to produce progeny retroviruses). For example, supernatant isolated from cells transduced by the vectors and contacted with a test cell should not result in localization of the fluorescent protein in the test cell.

In a fourth aspect of the present invention, methods of introducing nucleotide sequences into a cell are provided. In one embodiment, the method includes contacting, or transducing, a cell permissive for either filoviral entry, or entry of a virus having at least two different viral glycoproteins in its lipid bilayer such as a togavirus, with a retrovirus that has been pseudotyped with a filoviral glycoprotein or at least two different viral glycoproteins, such as togaviral glycoproteins, as described above that includes the desired nucleotide sequence in its genome. When the nucleotide sequences encode a desired protein, the cell is selected so that it also preferably allows expression of the selected nucleotide sequence. The level of transduction may be obtained by assaying methods known to the skilled artisan, and include assaying for the protein of interest encoded by the introduced nucleotide sequences or assaying for the presence of the nucleotide sequences. Viruses having at least two different viral glycoproteins in their lipid bilayer have a broad host range. For example, as togaviruses are pantropic (i.e., can invade, or infect, many different cell types with no special affinity for any particular cell type), a wide variety of permissive cell types well known to the art may be chosen for use in the method, including for example, skin cells, muscle cells, fibroblasts, fat cells and central nervous system cells.

Other viruses having at least two viral glycoproteins in their lipid bilayer include those previously described above. Cells permissive for these viruses are well known to the skilled artisan. Similarly, as filoviruses infect a broad range of cells, a wide variety of cells known to the art that are permissive for filovirus entry may also be selected, including, for example, kidney cells, liver cells, muscle cells and fibroblasts.

In a fifth aspect of the present invention, methods of screening agents effective in blocking viral entry into a cell are provided. The methods allow for direct screening as the viral entry step can be detected in the method. If such agents were tested with a wild type virus, for example, multiple rounds of replication may occur and steps other than viral entry may thus be affected (e.g., such as replication of RNA, production of proteins, etc.). In such a case, one would not know if the agent affects the entry step or some other, indirect step. Thus, the present method allows for direct quantitation of viral entry as compared to remote quantitation.

In one embodiment of the methods of the present invention, a method includes (a) treating a pseudotyped retrovirus having a retroviral capsid, a lipid bilayer that surrounds the retroviral capsid, at least two different viral glycoproteins disposed in its lipid bilayer and a nucleotide sequence encoding a marker, preferably a visually detectable marker (or one that is capable of visual detection as described above) that is enclosed within the retroviral capsid, with an agent effective in blocking entry into a cell of the virus having at least two different viral glycoproteins in its lipid bilayer to form a treated pseudotyped retrovirus; (b) treating a cell permissive for entry of a virus having at least two different viral glycoproteins in its lipid bilayer with the treated pseudotyped retrovirus; and (c) identifying cells having the desired marker. In one embodiment, the retrovirus may have togaviral glycoproteins disposed in its lipid bilayer, and the cells are permissive for togaviral entry. In alternative embodiments, the retrovirus may have a filoviral glycoprotein, such as a Marburg virus glycoprotein, disposed in its lipid bilayer, wherein the cells that are treated are permissive for Marburg virus entry.

Cells that are advantageously used in a method of screening agents effective in blocking viral entry into a cell are those that are permissive for entry of the specific virus, and will therefore depend on the virus used. Cells permissive for entry of a virus having at least two different viral glycoproteins disposed in its lipid bilayer are the same as recited in the method of introducing nucleotide sequences into a cell as discussed above. Similarly, cells permissive for Marburg virus entry include those described above used in the method of introducing nucleotide sequences into a cell. If it is not known whether a cell is permissive for viral entry, this can readily be determined by the skilled artisan using routine procedures. One way of determining whether a cell is permissive for viral entry is to transduce the cell with a pseudotyped retrovirus of the present method encoding a marker, and cells that have the marker may be identified by methods known to the art. The marker may be a visually detectable marker, such as the green fluorescent protein or β-galactosidase (i.e., one that gives rise to a visually detectable marker) described above. The selected cell should also allow for expression of the gene products encoded and carried on the viral genome.

A wide variety of agents may advantageously be screened in the present invention, including, immunological agents such as monoclonal and/or polyclonal antibodies. For example, monoclonal antibodies or polyclonal antisera against $E_2$, or other viral glycoproteins, may advantageously be used. Various pharmacological agents may also be screened in the present method in the same way, and include proteins, peptides or various chemical agents.

In one preferred method, the vector, in (a) above, is treated, or incubated with, the agent for a time period sufficient for interaction of the agent with the viral glycoprotein. Although this time period may vary depending on the nature of the agent and the viral glycoprotein, agents effective in blocking viral entry tend to effectively interact with the glycoprotein in a period of about 10 to about 60 minutes.

In (b), the cell is incubated, or contacted, with the treated pseudotyped retrovirus for a time period sufficient for viral entry. This time period may vary, depending on the specific cell type chosen and the specific viral glycoprotein present in the lipid bilayer of the pseudotyped retrovirus as the skilled artisan knows. However, the time period can typically range from about 1 to about 6 hours, but is typically about 1 to about 2 hours.

Cells having the desired marker may be identified in (c) by observing the presence of the marker. Any of the visually detectable markers previously described above may be utilized in the method. However, a preferred marker is the *Aequorea Victoria* green fluorescent protein. Cells into which this marker has been introduced may be identified and separated from cells without the marker (cells not transduced by the retrovirus) by fluorescence-activated cell sorting as described above.

Furthermore, yet another embodiment of a method of screening agents effective in blocking viral entry into a cell includes (1) treating a cell permissive for entry of a virus having at least two different viral glycoproteins in its lipid bilayer with the agent to form a treated cell; (2) contacting the treated cell with a pseudotyped retrovirus having a retroviral capsid, a lipid bilayer that surrounds the retroviral capsid, at least two different viral glycoproteins disposed in its lipid bilayer and a nucleotide sequence encoding a marker, preferably a visually detectable marker (or one that is capable of visual detection as described above), that is enclosed within the retroviral capsid; and (3) identifying cells having the desired marker. As above, the retrovirus may have togaviral glycoproteins disposed in its lipid bilayer, and the cells are permissive for togaviral entry. In alternative embodiments, the retrovirus may have a filoviral glycoprotein, such as a Marburg virus glycoprotein, disposed in its lipid bilayer, wherein the cells that are treated are permissive for Marburg virus entry. The cells and agents advantageously used in this embodiment are the same as described in the previous embodiment.

In this alternative embodiment, the cells in (1) above are treated, or incubated with, the agent for a time period sufficient for interaction of the agent with the cell to form a treated cell. Although this time period may vary depending on the nature of the agent and the cell, agents effective in blocking viral entry tend to effectively interact with the cell in a period of about 1 hour.

In (2), the treated cell is incubated, or contacted, with the pseudotyped retrovirus for a time period sufficient for viral entry. The time period may vary, depending on the specific cell type chosen and the specific viral glycoprotein in the lipid bilayer of the pseudotyped retrovirus as the skilled artisan knows. However, the time period ranges from about 1 to about 6 hours, but is typically about 1 to about 2 hours.

Cells having the desired marker may be identified in (3) by the same method as described in (c) of the previous embodiment.

In a sixth aspect of the present invention, kits for forming inventive pseudotyped retroviruses are provided. The kits include a first nucleotide sequence encoding a retroviral Gag polypeptide, a second nucleotide sequence encoding a retroviral Pro polypeptide, a third nucleotide sequence encoding a retroviral Pol polypeptide and a fourth nucleotide sequence encoding at least one viral glycoprotein. In one embodiment of the invention, the fourth nucleotide sequence encodes at least two different viral glycoproteins, such as togaviral glycoproteins and preferably alphaviral glycoproteins. In alternative embodiments, the fourth nucleotide sequence encodes a filoviral glycoprotein, preferably a Marburg virus glycoprotein. The sequences and methods of obtaining such sequences are discussed above. In general, the kits include sterile packaging which secures the various kit components in spaced relation from one another sufficient to prevent breakage of the components during handling of the kit. For example, it is a common practice to utilize molded plastic articles having multiple compartments or areas for holding the kit components in spaced relation.

The inventive pseudotyped retrovirus are further useful in methods of identifying cell surface receptors that allow viral entry. In one embodiment, an inventive pseudotyped retrovirus may be employed in a method that identifies cell surface receptors for a virus having at least two different viral glycoproteins disposed in its lipid bilayer. The method includes (a) constructing a cDNA library from a first cell that is permissive for entry of a virus having at least two different viral glycoproteins disposed in its lipid bilayer; (b) transfecting a second cell with a cDNA-carrying vector wherein the second cell is non-permissive or semi-permissive for entry of a pseudotyped retrovirus that includes a retroviral capsid, a lipid bilayer wherein the lipid bilayer surrounds the retroviral capsid, at least two different viral glycoproteins disposed in its lipid bilayer and a nucleotide sequence encoding a desired marker wherein the nucleotide sequence is enclosed within the retroviral capsid; (c) transducing the second cell with the pseudotyped retrovirus; (d) identifying cells having the marker; and (e) identifying the cDNA insert in the transduced cell. In alternative embodiments, the cDNA library is constructed from a first cell permissive for entry of a Marburg virus and the second cell is transduced with a retrovirus pseudotyped with the Marburg virus glycoprotein.

In a preferred method, the first cell is permissive for togaviral entry, further preferably alphaviral entry, and the second cell is transduced with a retrovirus pseudotyped with togaviral glycoproteins, preferably alphaviral glycoproteins.

In (a), a cDNA library may be constructed by methods well known to the skilled artisan as described in *Current Protocols in Molecular Biology*, John Wiley and Sons, edited by Ausubel et al. (1988). For example, mRNA may be isolated from the first cell by breaking the cell membrane and extracting and purifying the mRNA by known methods. The mRNA may be used as a template to form cDNA, which may then be cloned into various vectors as described above, such as plasmid vectors, by use of various restriction enzymes and DNA ligase as known in the art. Bacterial cells, or other similar cells, may be transfected with the expression vectors to form the cDNA library.

The first cell may be chosen from the cells permissive for entry of a virus having at least two different viral glycoproteins disposed in its lipid bilayer, such as an alphavirus, or a virus having a filoviral glycoprotein disposed in its lipid bilayer, such as a Marburg virus glycoprotein, or other filovirus glycoprotein as described above.

In (c), the second cell may be transduced with a pseudotyped retrovirus having a nucleotide sequence encoding a desired marker as described above in the embodiment described above of the method for screening agents effective in blocking viral entry into a cell and in (d), the transduced cells may be identified by methods discussed above, such as fluorescence activated cell sorting.

The second cell may be selected from non-permissive cells, preferably mammalian, known in the art. For example, in the case of the pseudotyped retrovirus that includes at least two viral glycoproteins disposed in its lipid bilayer, such as those from the Ross River virus, non-permissive cells include chicken embryo fibroblasts. One skilled in the art may also determine what other cells are non-permissive for alphaviruses, such as the Ross River virus, and the filoviruses, such as Marburg or Ebola virus, by the methods described herein as well as other methods known to the art.

The cDNA insert in the transduced eukaryotic cell may be identified and recovered by known methods, including amplifying known sequences in the cDNA-containing plasmids by PCR.

Reference will now be made to specific examples illustrating the compositions and methods above. It is to be understood that the examples are provided to illustrate preferred embodiments and that no limitation to the scope of the invention is intended thereby.

EXAMPLE 1

Cells and Cell Culture

E86nlslacZ cells, Baby Hamster Kidney (BHK) cells, and mouse NIH3T3 fibroblasts were grown in Dulbecco's Modified Eagle Media (D-MEM, Sigma) with 10% Calf Serum (Gibco-BRL), 0.1 mg/ml streptomycin (Sigma) and 10 U/ml penicillin (Sigma)(D-MEM CS/PS). E86nlslacZ cells are NIH 3T3 cells that express MMLV capsid proteins, produced as known in the art and as described in Taylor, G. M. and Sanders, D. A. (1999) *Mol. Biol. of the Cell* (1999), in press, were constructed by stably transfecting GP+E86 cells of Markowitz et al. (1988) *J. of Virol.* 62:1120–1124 with MFG.S-nlsLacZ. MFG.S-nlsLacZ is a retroviral vector encoding a nuclear localized β-galactosidase activity, produced as known in the art and as described in Ory, et al. (1996) *PNAS USA* 93:11400–11406.

Human HeLa, ΦNX cells, gpGFP and gpnlslacZ cells were grown in D-MEM FBS/PS). ΦNX packaging cells are second generation human embryonic kidney 293T cells transfected with MMLV gag and pol genes as described in Grignani et al. (1998) *Cancer Res.,* 58:14–19 and Pear et al., (1993) *PNAS USA,* 90:8392–8396. gpGFP cells are obtained by transfecting ΦNX cells with retroviral vector MFG.S-GFP-S65T, a retroviral vector encoding the *Aequorea victoria* green fluorescent protein S65T mutant as described in Taylor, G. M. and Sanders, D. A. (1999) *Mol. Biol. of the Cell* (1999), in press. gpGFP cells therefore produce envelope-deficient replication-incompetent MMLV particles carrying MFG.S-GFP-S65T. gpnlslacZ cells were developed in our laboratory by cotransfecting MFG.S-nlsLacZ and pJ6 Ωpuro [constructed as described in Morgenstern and Land (1990), *Nucleic Acids Res.,* 18:1068] into ΦNX cells, growing transfected cells in D-MEM FBS/PS supplemented with 2 µg/ml puromycin (Sigma) and antibiotic-resistant colonies were isolated and screened for the production of high-titer replication-incompetent virus resulting from transient transfection with penv1 min, a vector that encodes the wild type MMLV envelope protein [as described in Taylor, G. M. and Sanders, D. A. (1999) *Mol. Biol. of the Cell* (1999), in press].

VSV-G pseudotyped retrovirus-producing 293GPGnlslacZ cells, constructed as described in Ory, et al. (1996) *PNAS USA* 93:11400–11406, were grown in D-MEM FBS/PS supplemented with 2 µg/ml puromycin and 1 µg/ml tetracycline (Sigma). As expression of the VSV-G protein in these cells is repressed by the presence of tetracycline in the medium, forty-eight hours before collection of pseudotyped virus the medium in which the 293GPGnlslacZ cells were grown was replaced with D-MEM FBS/PS.

All cells were grown at 37° C. and under 5% $CO_2$. Moreover, the cells were grown at a density of no more than about 50% confluency and the medium was changed at intervals sufficient to maintain the pH of the medium at about 7.

EXAMPLE 2

Generation of Cell Lines Transiently Producing RRV-MMLV Pseudotyped Retrovirus

RRV Glycoprotein Expression Plasmid Construction

The region encoding the Ross River virus envelope glycoproteins was amplified from pRR64, a plasmid which contains the full-length Ross River viral genome [full-length sequence described in Faragher et al., (1988), *Virology* 163:509–526] as described in Kuhn et al. (1991), *Virology* 182:430–41, by the polymerase chain reaction using Pfu polymerase and two primers complementary to the viral genome at nucleotides 8375–8386 (5'-CGGGATCCACCAT-GTCTGCCGCGCT-3') (SEQ ID NO:7) and 11312–11330 (5'-CGCTCTAGATTACCGACGCATTGTTATG-3') (SEQ ID NO:8) [the amplified sequences from plasmid pRR64 are shown in (SEQ ID NO:1) beginning at nucleotide 3, and an additional "at" sequence (nucleotides 1 and 2 of (SEQ ID NO:1)) was added at the 5' end of the pRR64 sequence]. The amplified fragment, which contained the RRV $E_3$-$E_2$-6K-$E_1$ coding region, was digested with the restriction endonucleases Bam HI and XbaI and ligated into BamHI and XbaI sites of pBacPac, a Baculovirus expression vector available from Clontech. The resulting plasmid was digested with BamHI and XbaI, and the fragment containing the RRV $E_3$-$E_2$-6K-E, coding region was ligated into the BamHI and XbaI sites in the pcDNA3 mammalian expression vector available from Invitrogen. The resulting plasmid was designated pRRV-$E_2$-$E_1$. (SEQ ID NO:1) shows the amino acid sequence of the $E_3$-$E_2$-6K-E, polypeptide.

Transient Transfection Procedure

In preparation for transfection, $0.5\times10^6$ ΦNX cells, or gpnlslacz cells, were washed with PBS (137 mM NaCl, 27 mM KCl, 4.3 mM $Na_2HPO4$, 1.47 mM $K_2HPO4$, pH 7.4) prior to incubation with 2 ml Opti-MEM (Gibco-BRL) for 30 minutes at 37° C. in a 5% $CO_2$ atmosphere. 2 μg of pRRV-$E_2$-$E_1$ and 2 μg of MFG.S-GFP-S65T was incubated with 300 ml Opti-MEM and 24 ml lipofectAMINE™ (Gibco-BRL) for 30 minutes at room temperature prior to dilution with 2.4 ml Opti-MEM. The resulting mixture was incubated with the cells for seven hours at 37° C. in a 5% $CO_2$ atmosphere. Medium was replaced with DMEM FBS/PS for a further 48-hour incubation at 37° C. in a 5% $CO_2$ atmosphere before collection of the supernatant medium for analysis of the transduction capacity of and level of glycoprotein incorporation into viral particles. When the gpnlslacZ cells were transfected, a similar protocol was followed except that the transfected DNA consisted solely of 4 μg of pRRV-$E_2$-$E_1$.

Transduction by Recombinant Retroviruses

HeLa, BHK and NIH 3T3 cells were transduced by the following method. Supernatant medium from recombinant-virus-producing cells was filtered through a 0.45 μm filter, mixed with hexadimethrine bromide (Sigma) (final concentration 8 μg/ml) and incubated with cells for five hours at 37° C. in a 5% $CO_2$ atmosphere. The recombinant virus-containing medium was then replaced with D-MEM CS/PS medium. Cells transduced with MFG.S-GFP-S65T were washed 48 hours after infection with PBS, then lifted from the plate with PBS containing 1 mM EDTA. The cells were then analyzed with a Coulter XL-MCL Flow Cytometer using a 525 nm band-pass and a 488 nm air-cooled argon laser. The level of glycoprotein incorporation into viral particles was determined by Western blotting as described in Example 4.

Analysis

Cell have been constructed that produce infectious pseudotyped virus containing the glycoproteins from the Ross River virus. The titer of virus was found to be $1\times10^3$ TU/ml supernatant. The cells were able to produce the pseudotyped retrovirus for a period of 48 hours. As MMLV only infects mouse cells such as NIH 3T3 and the Ross River virus glycoprotein-pseudotyped retrovirus is able to infect NIH 3T3 cells, as well as BHK (hamster) and HeLa (human) cells, it has clearly been demonstrated that the host range of these retroviruses is increased by incorporation of the Ross River glycoproteins in the virus.

This example also shows that at least two different viral glycoproteins, each having a different membrane-spanning domain, can be incorporated into a retroviral particle (i.e., a retrovirus).

EXAMPLE 3

Generation of Stable Cell Lines Producing RRV-MMLV Pseudotyped Retrovirus

Stable Transfection Procedure $0.5\times10^6$ ΦNX or gpnlslacZ cells were transfected following the protocol in Example 2, except that the DNA that was transferred was only 8 μg of pRRV-$E_2$-E, and 0.4 μg of plasmid pJ6 Ωpuro coding for puromycin resistance [Morgenstern and Land, *Nucleic Acids Res.* 18, 1068 (1990)] and the DNA mixture contained 48 μl lipofectAMINE™ and 600 μl Optim-MEM. Selection with medium containing 2 μg/mL puromycin began at 48 hours post-transformation. Clonal colonies of cells were isolated after two weeks of selection. The resulting cell lines derived from the ΦNX cells were designated SafeRR and the resulting cell lines derived from the gpnlslacZ cells were designated SafeRRnlslacZ.

Titer was measured by infection of NIH3T3 cells as described below. Infection occurred in the presence of 8 μg/ml polybrene and infectious supernatant was changed to media without polybrene 5 hours post-infection.

Transduction by Recombinant Retroviruses

The same protocol of Example 2 was followed, except that forty-eight hours after the infection, the cells transduced with virus bearing MFG.S-nlslacZ were fixed with 0.5% glutaraldehyde (Sigma) and then incubated with 1 mg/ml of the β-galactosidase detection reagent 5-bromo-4-chloro-3-indolyl-β-D-galactopyranoside (X-gal, Fisher) in a staining buffer (1 mM $MgCl_2$, 50 mM $K_3Fe(CN)_6$ and 50 mM $K_4Fe(CN)_6$) for 3 hours prior to the determination of the proportion of blue cells as provided in Sanes, et al. (1986), *Embo J.,* 5:3133–3142.

Analysis

Cells that permanently produce the above pseudotyped retroviruses have been constructed. SafeRR cells were found to produce pseudotyped retrovirus at a titer of $1\times10^3$ TU/ml supernatant. SafeRR-nlslacZ cells were found to produce pseudotyped retrovirus at a titer of about $1\times10^5$ TU/ml supernatant. SafeRR cells may be advantageous in introducing desired nucleotide sequences into a cell. Another advantage is that the expression of the Ross River virus glycoproteins are not toxic to the cells.

EXAMPLE 4

Immunodetection of Incorporation of RRV-$E_2$ into Pseudotyped Retrovirus Produced by SafeRR-nslacZ Cells This example demonstrates that the recombinant retrovirus contains the Ross River glycoproteins.

Supernatant medium from a 10 cm tissue-culture dish of confluent SafeRRnlslacZ cells (described in Example 3), or precursor gpnlslacZ cells (described in Example 1), was passed through a 0.45 μm filter and spun through a 30% sucrose cushion at 25K rpm for 2.5 hours in a Beckman 50.2 titanium rotor. Material collected through the centrifugation was suspended in SDS-PAGE buffer (0.05% bromophenol blue, 0.0625 M Tris-HCl pH 6.8, 1% SDS, 10% glycerol). Cell lysates were prepared by washing cells with 10 ml PBS followed by 2 ml cell lysis buffer (50 mM Tris-HCL, 5 mM EDTA, 150 mM NaCl, 1% Triton X-100). Aliquots of total lysed material were mixed with SDS-PAGE buffer and analyzed electrophoretically. PAGE-separated proteins were transferred to nitrocellulose membranes at 44 mA for 2 hours in transfer buffer (25 mM Tris, 192 mM glycine, 20% methanol). Membranes were blocked with 5% powdered milk in washing solution (20 mM Tris-HCl, pH7.6, 137 mM NaCl, 0.1% Tween-20). Blocked membranes were reacted with pAbE2 (anti-Ross River $E_2$ rabbit polyclonal antiserum; provided by Richard Kuhn and produced by methods known to the art) at a 1:5000 dilution for two hours and goat anti-rabbit Horseradish Peroxidase (HRP)-linked secondary antibody (Chemicon, 1 mg/ml) at a 1:5000 dilution for thirty minutes. Western blots were visualized with Enhanced Chemiluminescent Reagents (Amersham Pharmacia Biotech) by methods known in the art.

Analysis

In order to clarify that $E_2$-$E_1$ were incorporated into the MMLV particles and could be mediating the infection observed in Example 3, both virus producing cells and infectious supernatants were analyzed by SDS-PAGE and Western blotting with a polyclonal $E_2$ antiserum.

As seen in FIG. 1, a 50 kDa and a 60 kDa immunoreactive protein were present in a lysate of SafeRRnlslacZ (express RRV $E_2$-$E_1$ pseudotyped MMLV). These are appropriate masses for $E_2$ and unprocessed $E_2$-$E_3$. Western analysis of virus collected from infectious supernatant revealed only the fully processed 50 kDa protein.

EXAMPLE 5

Formation of Syncytia in Stable SafeRR-nlslacZ Cell Lines at Acidic pH

This example shows that SafeRR-nlslacZ cell lines are capable of forming syncytia at acidic pH, implying that entry of alphavirus into cells is dependent on the low pH environment normally found in endosomes.

SafeRR-nlslacZ or ΦNX cells, obtained as described in Examples 3 and 1, respectively, were grown to near confluence, washed with PBS and treated with fusion buffer [PBS containing 10 mM 2-(N-morpholino)ethane sulfonic acid and 10 mM HEPES adjusted to pH 5.5] for one minute. The low pH solution was replaced with D-MEM FBS/PS, then cells were incubated in a $CO_2$ incubator at 37° C., and the cells were stained with Giemsa solution 5 hours after treatment and photographed.

Analysis

Figure 2A:
FIG. 2 depicts Giemsa solution-stained SafeRR-nlslacZ cells (Panel A, FIG. 2A) and ΦNX cells (Panel B, FIG. 2B) after being incubated at room temperature for one hour with pH 5.5 fusion buffer and grown in D-MEM FBS/PS culture medium for four hours as described in Example 5. Panel C (FIG. 2C) depicts Giemsa solution-stained SafeRR-nlslacZ cells treated in a similar manner with the exception that they were exposed to pH 7 fusion buffer instead of pH 5.5 fusion buffer.
Figure 2B:
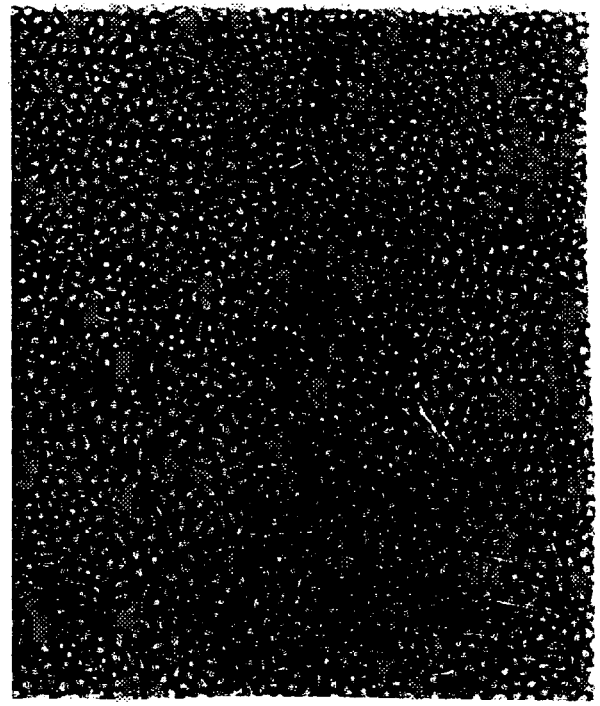
Figure 2C:
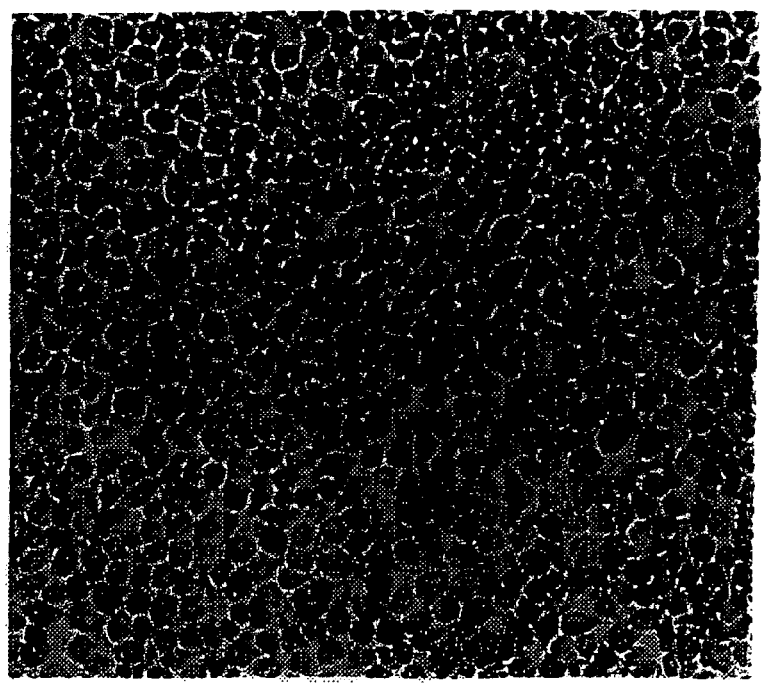

As seen in FIG. 2A, syncytia are detectable. No syncytia were observed in the treated ΦNX cells that are shown in FIG. 2B. It is seen in FIG. 2C that syncytia are also not detected when the SafeRR-nlslacZ cells are incubated in pH 7 fusion buffer. These results, indicating that Ross River virus glycoprotein-promoted membrane fusion is triggered by an acidic medium, are consistent with the data obtained by other laboratories that indicate the entry of alphavirus is dependent upon the low pH environment normally found in endosomes [other data discussed in Strauss and Strauss, (1994) *Microbiol. Rev*, 58:491–562].

EXAMPLE 6

Effect of Lysosomotropic Weak Bases on Infection by RRV-MMLV Pseudotyped Retrovirus This example shows that the RRV-MMLV pseudotyped retrovirus enters cells through an endocytic pathway.

Figure 3B:
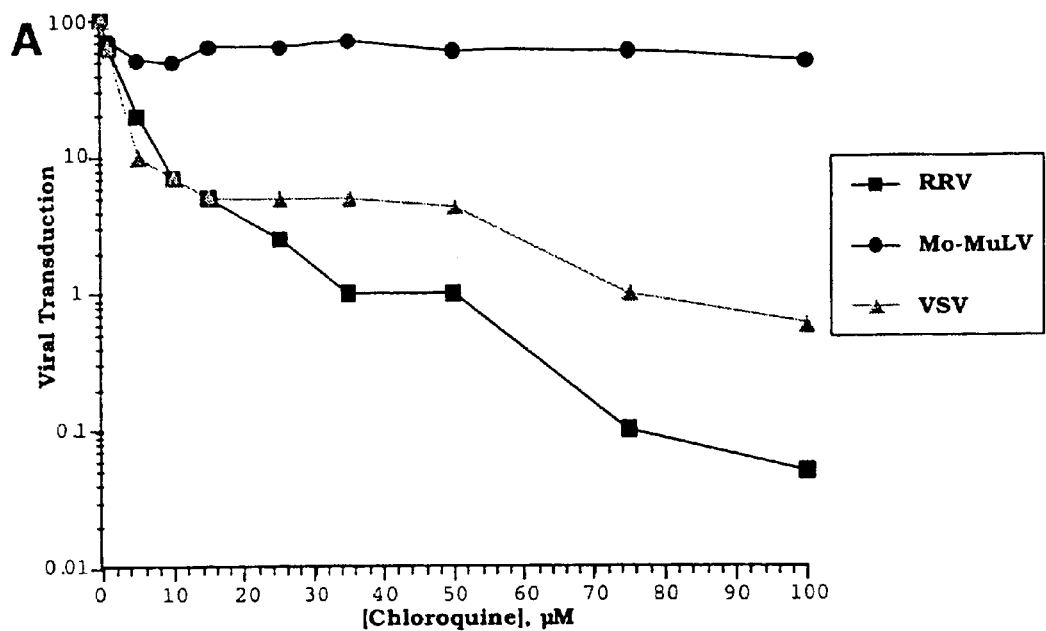
FIG. 3B, shows the effect of chloroquine. RRV, pseudotyped virus obtained from supernatants of SafeRR-nlslacZ cells; Mo-MuLV, wild type Moloney murine leukemia virus expressing the env glycoprotein; VSV; Moloney murine leukemia virus pseudotyped with vesicular stomatitis viral glycoprotein G.

NIH 3T3 cells were pretreated for one hour with various concentrations of ammonium chloride or chloroquine in PBS as seen in FIG. 3. Medium containing $1.5 \times 10^5$ TU/ml of supernatant of either wild type MMLV, VSV-G pseudotyped retrovirus or Ross-River $E_2$-$E_1$ pseudotyped retrovirus (produced by SafeRRnlslacZ cells) containing various concentrations of bases (as seen in FIG. 3) as well as 8 µg/ml polybrene was incubated with the cells in a $CO_2$ incubator at 37° C. The virus-containing medium was replaced with D-MEM CS/PS 6 hours after infection. The cells were stained with a β-galactosidase detection reagent (X-gal) at 48 hours post infection, and blue cells were counted. The results are shown in FIG. 3.

Analysis

Figure 3A:
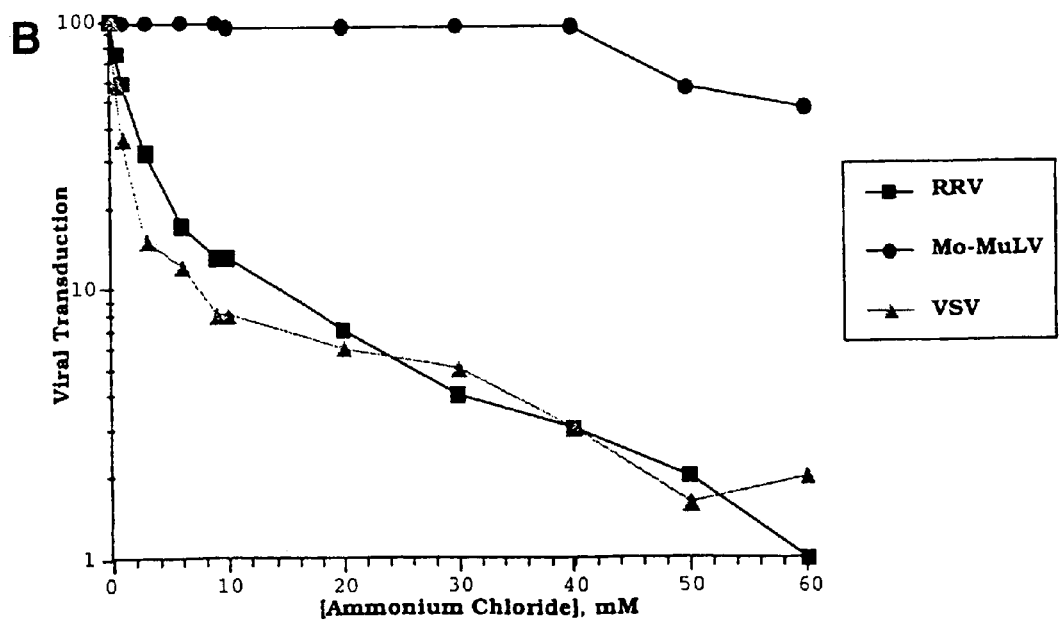
FIG. 3A, shows the effect of ammonium chloride and right panel, B.

Ammonium chloride and chloroquine inhibit the acidification of endosomes and inhibit cellular entry of viruses that are taken up by endocytosis and that require exposure to low pH for virus-cell membrane fusion to occur as reported in Marsh and Helenius, *Adv. Virus Res.* (1989), 36:107–151. MMLV entry is known not to involve low pH-induced virus-cell membrane fusion and infection by VSV-G pseudotyped retrovirus is known to involve low pH-induced virus-cell membrane fusion. These retroviruses therefore served as controls. The results show that chloroquine only partially affects wild type MMLV entry as seen in FIG. 3A, and that both chloroquine and ammonium chloride inhibit VSV-G pseudotyped retrovirus entry. It can therefore be concluded that the dramatic inhibition of transduction by Ross River glycoprotein-pseudotyped viruses in the presence of ammonium chloride and chloroquine is a direct effect upon entry, as all of the macromolecules required for the other necessary processes (viral uncoating, reverse transcription, integration, etc.) are identical with those contained in the relatively uninhibited MMLV-Env-bearing viruses. This example illustrates one of the advantages of the inventive pseudotype system of the present invention; the effects of an experimental manipulation on viral entry into a cell may be specifically investigated independent of any effects on other steps in replication.

EXAMPLE 7

Neutralization of MMLV Pseudotyped with RRV $E_2$-$E_1$ Coding Region

This example shows that retroviruses pseudotyped with the Ross River virus E2-E1 are inhibited from entering a cell when pre-incubated with antibodies against E2.

Supernatants from SafeRR-nlslacZ or wild type MMLVnlsLacZ (MMLV that includes RNA encoding β-galactosidase and the env gene proteins) producing cells were incubated with dilutions of Ross River virus monoclonal 10C9 [produced as described in Smith, (1995) *PNAS USA* 92:10648–10652] in ascites fluid or dilutions of Ross River virus polyclonal (pAbE2) antiserum (provided by Richard Kuhn and produced by methods known to the art) prior to infection of NIH3T3 cells. No significant inhibition of infectivity was observed in wild type MMLVnlsLacZ while a 60% inhibition of infectivity of RRV-MMLVnlsLacZ was observed at a 1:500 dilution of polyclonal antiserum. Inhibition was most significant with monoclonal 10C9, which binds to the cell receptor binding region on RRV $E_2$ (Smith et al., *Proc Natl Acad Sci USA* 92, 10648–10652 (1995)). For example, a 70% inhibition of infectivity was observed in supernatant from SafeRR-nlslacZ cells with a 1:500 dilution of ascites fluid containing monoclonal 10C9.

EXAMPLE 8

Generation of Cell Lines Transiently Producing Ebola-MMLV Pseudotyped Retrovirus Including Nucleotide Sequences Encoding GFP in its Genome This example shows production of cell lines that transiently produce MMLV pseudotyped with Ebola-Zaire glycoprotein.

pEZGP1 was produced by cloning into the polylinker of plasmid pcDNA3 nucleotide sequences corresponding to nucleotides 6029–8253 [sequences 6029–8253, corresponding to nucleotides 132–2354 described in Genbank as Accession Number U23187, are shown in SEQ ID NO:3 from the Ebola Zaire virus genome, with the exception that an additional "a" has been inserted between nucleotides 1027 and 1028 in SEQ ID NO:3 compared to the Genbank sequence] from the complete Ebola Zaire genome [described in Sanchez et al. (1993) Virus Res. 29(3):215–240] obtained by digestion of the MP1153 plasmid provided by Dr. Anthony Sanchez with Eco RI and HindIII. SEQ ID NO:4 shows the amino acid sequence of the Ebola Zaire glycoprotein.

gpGFP cells were transiently transfected with pEZGP1 using lipofectAMINE™ (Gibco, BRL) and Opti-MEM media (Gibco, BRL). The gpGFP cells were plated at 5×10⁵ cells/60 mm plate 24 hours prior to transfection. The cells were washed and incubated for 30 minutes at 37° C. with 2 ml of Opti-MEM media. The DNA-LipofectAMINE™-Opti-MEM mixture (4 µg DNA, 24 µl lipofectAMINE™, and 300 µl Opti-MEM media) was incubated for 30 minutes at 25° C. After the 30 minute incubations, 2.4 ml of Opti-MEM media was added to the DNA-lipofectAMINE™ mixture. The resulting solution was layered onto the gpGFP cells. Eight hours later, the transfection mixture was removed and the cells were incubated with DMEM FBS/PS for 40 hours. The supernatant medium was filtered through a 0.45 µm filter and then incubated with 1×10⁶ NIH 3T3 cells in the presence of 8 µg/ml polybrene for 4 hours. The recombinant-virus-containing medium was then replaced with D-MEM CS/PS. Forty-eight hours later the cells were removed from the plate, suspended in 1×PBS containing 1 mM EDTA, and analyzed by flow cytometry with a Coulter XL-MCL Flow Cytometer, using a 525 nm band-pass filter and a 488 nm air-cooled argon laser.

Analysis

Cell have been constructed that produce infectious pseudotyped virus containing glycoproteins from the Ebola Zaire virus. The titer of virus was found to be 4.5×10⁴ TU/ml of supernatant. The cells were able to produce the pseudotyped retrovirus for a period of about 24 hours.

EXAMPLE 9

Generation of Stable Cell Lines Producing Ebola-MMLV Pseudotyped Retrovirus gpGFP cells were stably transfected with pEZGP1. gpGFP cells were plated at 5×10⁵ cells/60 mm plate 24 hours prior to transfection. The cells were washed and incubated for 30 minutes at 37° C. with 2 ml of Opti-MEM media. The DNA-LipofectAMINE™-Opti-MEM mixture (8 µg of mutant DNA, 0.4 µg of pJ6 Ωbleo, 48 µl lipofectAMINE™, and 300 µl Opti-MEM media) was incubated for 30 minutes at 25° C. After the 30 minute incubations, 2.4 ml of Opti-MEM media was added to the DNA-LipofectAMINE™ mixture. The resulting solution was layered onto the gpGFP cells. Eight hours later the transfection mixture was removed and the cells were incubated with DMEM FBS/PS for 40 hours before transferring the cells to 10 cm plates at two different dilutions (1/10 and 1/100). The following day, the media was changed to D-MEM FBS/PS containing 200 µg/ml of Zeocin. Colonies appeared after two weeks and were picked for screening by an infectivity assay described below. The cell lines so produced were labeled "SafeEbola-GFP".

The supernatant medium from the cells was filtered through a 0.45 µm filter and then incubated with 1×10⁶ NIH 3T3 cells in the presence of 8 µg/ml polybrene for 4 hours. The recombinant-virus-containing medium was then replaced with D-MEM CS/PS. Forty-eight hours later the cells were removed from the plate, suspended in 1×PBS containing 1 mM EDTA, and analyzed by flow cytometry with a Coulter XL-MCL Flow Cytometer, using a 525 nm band-pass filter and a 488 nm air-cooled argon laser.

Stable cell lines that produce pseudotyped retrovirus not containing specific nucleotide sequences such as those encoding the green fluorescent protein were produced in the same manner, except the parent cell line to the gpGFP cells were used instead (i.e., ΦNX cells, human embryonic kidney cells transfected only with MMLV gag and pol nucleotide sequences). These cell lines were labeled "SafeEbola".

Figure 4A:
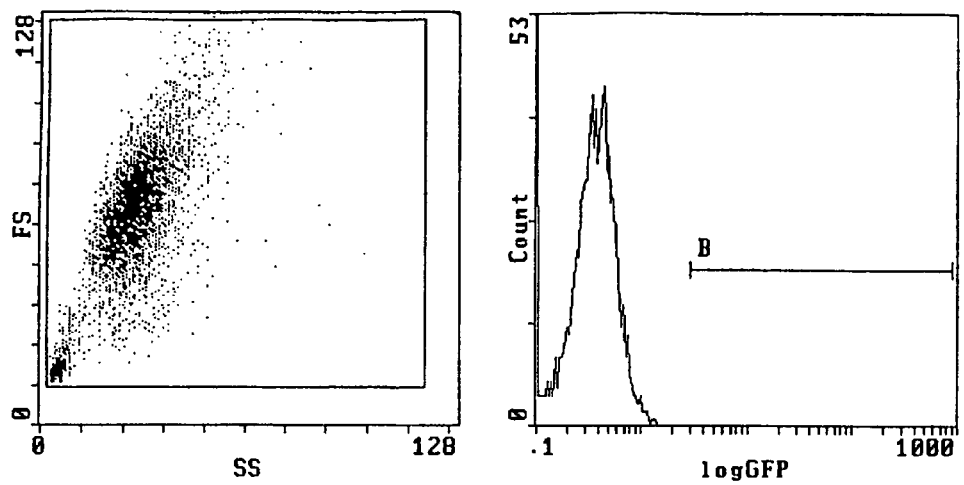
FIG. 4 shows fluorescence profiles of NIH 3T3 cells transduced with supernatant medium from ΦNX cells (top panel, A, FIG. 4A) or Safe-Ebola-GFP cells (bottom panel, B, FIG. 4B) according to the procedure outlined in Example 9.
Figure 4B:
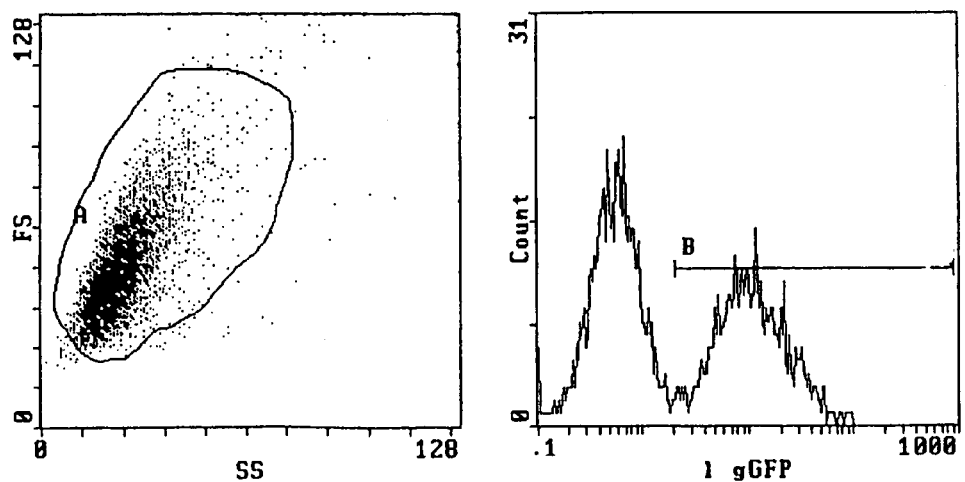

As seen in FIG. 4, lower panel B, cells (45.8% as determined by fluorescence activated cell sorting) transduced with pseudotyped retroviruses produced from SafeEbola-GFP cells exhibited detectable green fluorescence.

Analysis

Cell lines that stably produce MMLV virus pseudotyped with Ebola Zaire glycoprotein have been produced. The cells indefinitely produce the pseudotyped retrovirus. The glycoprotein used to form the pseudotyped retrovirus is not toxic. The cells require diligence in care (i.e., changing the media every two days) so that the pH does not drop and syncytia formation does not occur.

EXAMPLE 10

Formation of Syncytia in Stable SafeEBola-GFP Cell Lines at Acidic pH

This example shows that SafeEbola-GFP cell lines are capable of forming syncytia at acidic pH.

Figure 5A:
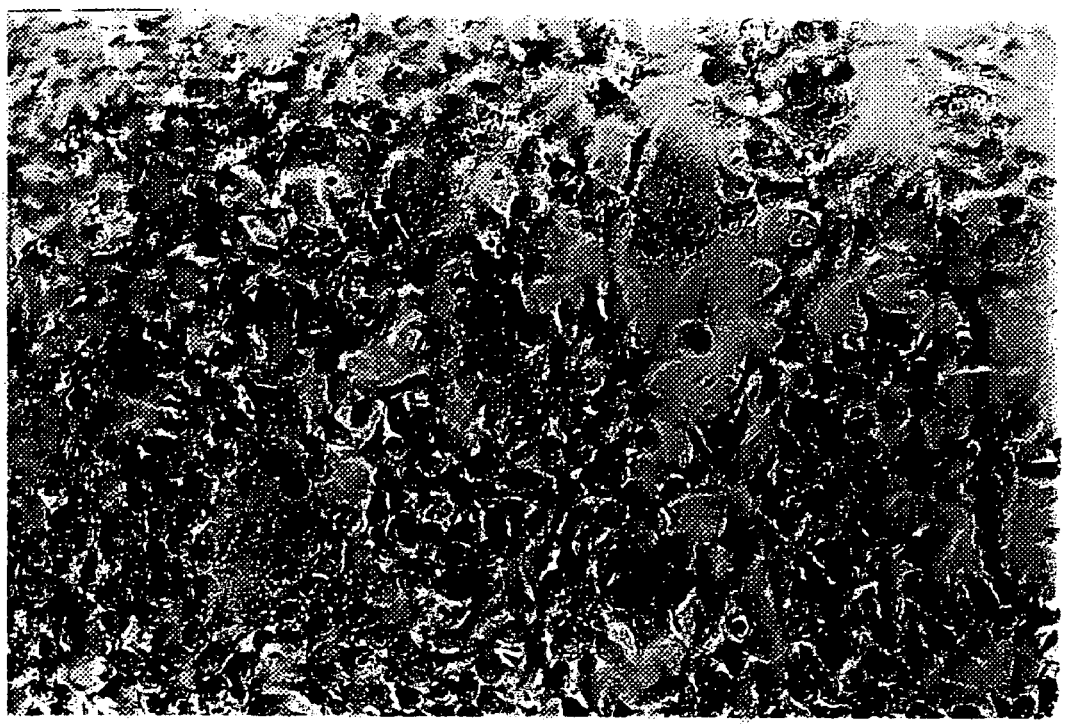
FIG. 5 depicts syncytia formation by packaging cells expressing Ebola glycoprotein. The cells were treated according to the protocol in Example 10. Top panel, A, (FIG. 5A) SafeEbola-GFP cells; Bottom panel, B, FIG. 5B, ΦNX cells.
Figure 5B:
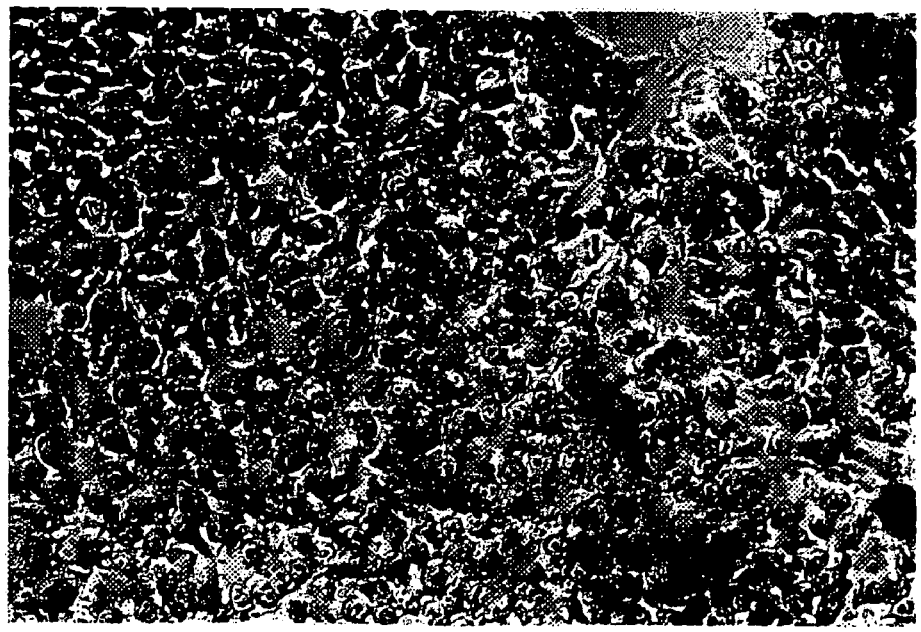

5×10⁵ SafeEbola-GFP cells or ΦNX cells, obtained as described in Examples 10 and 1, respectively, were plated on 60 mm tissue-culture dishes, grown to near confluence, washed with PBS and treated with fusion buffer [PBS containing 10 mM 2-(N-morpholino)ethane sulfonic acid and 10 mM HEPES adjusted to pH 5.5] for one minute. The low pH solution was replaced with D-MEM FBS/PS, incubated in a CO₂ incubator at 37° C., and the cells were stained with Giemsa solution 5 hours after treatment and photographed. As seen in FIG. 5A, the SafeEbola-GFP cell lines form syncytia at acidic pH, whereas no such syncytia are formed in ΦNX cells as seen in FIG. 5B.

EXAMPLE 11

Generation of Cell Lines Transiently Producing Marburg Virus Glycoprotein Pseudotyped Retrovirus Marburg Glycoprotein Expression Plasmid Marburg plasmid pMBGP1 was constructed from a plasmid from Hans-Dieter Klenk (Marburg, Germany). To construct this plasmid, the nucleotides 5931–8033 from the Marburg virus genome [the genomic nucleotide sequence HK Klenk, as delineated in Will et al. (1993), *J. Virol.* 67:1203–1210 and as seen in Genbank Accession Number Z12132 shown in (SEQ ID NO:5)] were cloned into the pSP72 plasmid (from Promega) under the control of the T7 promoter using SaII. The XhoI and Eco RI fragment of this plasmid was cloned into the XhoI and Eco RI polylinker sites of the mammalian expression vector pcDNA3. (SEQ ID NO:3) also shows the amino acid sequence of the Marburg virus glycoprotein.

Transient Transfection Procedure

The transient transfection protocol was identical to that recited in Example 8 (Ebola-glycoprotein transfection protocol), with the exception that, instead of pEZGP1, 4 µg of pMBGP1 was used.

Analysis

It has been shown that cell lines may be constructed that produce MMLV that is pseudotyped with the Marburg virus glycoprotein. The cell lines were found to produce the pseudotyped retroviruses at a titer of about $1.4 \times 10^3$ TU/ml of supernatant. The cells were able to produce the virus for a period of about 24 hours. In data not shown, it was found that NIH 3T3, BHK and HeLa cells can be efficiently transduced by this inventive pseudotyped retrovirus. This demonstrates the expanded host range of the pseudotyped retroviruses, which allows these pseudotyped retroviruses to be advantageously used to introduce desired nucleotide sequences into target cells.

EXAMPLE 12

Generation of Cell Lines Stably Producing Marburg Virus Glycoprotein Pseudotyped Retrovirus Stable Transfection Procedure The stable transfection protocol was identical to that recited in Example 9 (Ebola-glycoprotein transfection protocol), with the exception that 4 µg of pMBGP1 (described in Example 11) was used.

Analysis

It has been shown that cell lines may be constructed that stably, and thus indefinitely, produce MMLV that is pseudotyped with the Marburg virus glycoprotein. The cell lines were found to produce the pseudotyped retroviruses at a titer of about $1.9 \times 10^3$ TU/ml of supernatant. The glycoprotein incorporated into the lipid bilayer of the pseudotyped retroviruses is not toxic. Moreover, the cells require diligence in care (i.e., changing of the media every two days) so that the pH does not drop and syncytia formation does not occur.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

---

What is claimed is:

1. A pseudotyped-retrovirus-producing eukaryotic cell, comprising a eukaryotic cell including nucleotide sequences operatively encoding components of a pseudotyped retrovirus, said nucleotide sequences comprising:
   (a) a first nucleotide sequence operably encoding a retroviral Gag polypeptide;
   (b) a second nucleotide sequence operably encoding a retroviral Pro polypeptide;
   (c) a third nucleotide sequence operably encoding a retroviral Pol polypeptide; and
   (d) a fourth nucleotide sequence operably encoding at least two different Ross River alphaviral glycoproteins;
   wherein the retroviral Gag, Pol and Pro polypeptides are Moloney murine leukemia polypeptides.

2. The cell of claim 1, wherein said cell further comprises a fifth nucleotide sequence having a 5' and a 3' end, said fifth nucleotide sequence encoding a selected protein, said fifth nucleotide sequence operably linked at said 5' end to a first retroviral long terminal repeat sequence and operably linked at said 3' end to a second retroviral long terminal repeat sequence.

3. The cell of claim 2, wherein said selected protein is a marker.

4. The cell of claim 3, wherein said marker is a fluorescent protein.

5. The cell of claim 1, wherein said eukaryotic cell is a mammalian cell.

6. The cell of claim 5, wherein said mammalian cell is a human cell.

7. The cell of claim 1, wherein said cell produces a pseudotyped retrovirus having a lipid bilayer, said Ross River alphaviral glycoproteins disposed in said lipid bilayer.

8. The cell of claim 1, wherein said first, second, third and fourth nucleotide sequences are chromosomally-integrated.

9. A method of modifying a eukaryotic cell to prepare a pseudotyped-retrovirus-producing eukaryotic cell, said method comprising:

transfecting a eukaryotic cell with a first nucleotide sequence operably encoding a retroviral Gag polypeptide, a second nucleotide sequence operably encoding a retroviral Pro polypeptide, a third nucleotide sequence operably encoding a retroviral Pol polypeptide and a fourth nucleotide sequence operably encoding at least two different Ross River alphaviral glycoproteins;

wherein the retroviral Gag, Pol and Pro polypeptides are Moloney murine leukemia polypeptides.

10. The method of claim 9, wherein said first, second and third nucleotide sequences are operably linked to a promoter sequence.

11. The method of claim 9, wherein said first, second, third and fourth nucleotide sequences are chromosomally-integrated.

12. The method of claim 9, wherein said cell further comprises a fifth nucleotide sequence having a 5' end and a 3' end, said fifth nucleotide sequence encoding a selected protein, said fifth nucleotide sequence operably linked at said 5' end to a first retroviral long terminal repeat sequence and operably linked at said 3' end to a second retroviral long terminal repeat sequence.

13. A method of modifying a eukaryotic cell to prepare a pseudotyped-retrovirus-producing eukaryotic cell, said method comprising:

(a) transfecting a eukaryotic cell with a vector including a first nucleotide sequence encoding a retroviral Gag polypeptide, a second nucleotide sequence encoding a retroviral Pro polypeptide and a third nucleotide sequence encoding a retroviral Pol polypeptide, said first, second and third nucleotide sequences operably linked to a first promoter sequence, wherein the retroviral Gag, Pol and Pro polypeptides are Moloney murine leukemia polypeptides; and (b) transfecting said cell with a fourth nucleotide sequence encoding at least two Ross River alphaviral glycoproteins, said fourth nucleotide sequence operably linked to a second promoter sequence.

14. The method of claim 13, said method further comprising transfecting said cell with a vector including a fifth nucleotide sequence having a 5' and a 3' end, said fifth nucleotide sequence encoding a selected protein, said fifth nucleotide sequence operably linked at said 5' end to a first retroviral long terminal repeat sequence and operably linked at said 3' end to a second retroviral long terminal repeat sequence.

15. The method of claim 13, wherein said selected protein is a marker.

16. The method of claim 13, wherein said first, second, third and fourth nucleotide sequences are chromosomally-integrated.

17. A pseudotyped retrovirus, comprising:
(a) a Moloney murine leukemia virus capsid;
(b) a lipid bilayer, said lipid bilayer surrounding said Moloney murine leukemia virus capsid; and
(c) at least two different Ross River alphaviral glycoproteins disposed in said lipid bilayer.

18. The retrovirus of claim 17, said retrovirus further comprising a nucleotide sequence encoding a selected protein, said nucleotide sequence enclosed within said retroviral capsid.

19. A method of introducing a selected nucleotide sequence into a cell comprising transducing a cell with a pseudotyped retrovirus, said pseudotyped retrovirus comprising:
a selected nucleotide sequence;
a Moloney murine leukemia virus capsid;
a lipid bilayer surrounding said Moloney murine leukemia virus capsid; and
at least two different Ross River alphaviral glycoproteins disposed in said lipid bilayer;
wherein said cell is permissive for entry of a pseudotyped retrovirus having at least two different Ross River alphaviral glycoproteins in its lipid bilayer.

20. A kit for modifying a eukaryotic cell to prepare a pseudotyped-retrovirus-producing eukaryotic cell, said kit comprising:
(a) a first nucleotide sequence operably encoding a retroviral Gag polypeptide;
(b) a second nucleotide sequence operably encoding a retroviral Pro polypeptide;
(c) a third nucleotide sequence operably encoding a retroviral Pol polypeptide, wherein the retroviral Gag, Pol and Pro polypeptides are Moloney murine leukemia polypeptides; and
(d) a fourth nucleotide sequence operably encoding at least two different Ross River alphaviral glycoproteins; and
(e) means for transfecting a eukaryotic cell with said first, second, third, and fourth nucleotide sequences.

21. The method of claim 9, wherein the first, second, third, and fourth nucleotide sequences are provided on plasmid vectors.

22. The method of claim 21, wherein the first, second, and third nucleotide sequences are contiguous on a single plasmid vector.

23. The method of claim 22, wherein the fourth nucleotide sequence is on a different plasmid vector.

* * * * *

UNITED STATES PATENT AND TRADEMARK OFFICE
CERTIFICATE OF CORRECTION

PATENT NO. : 7,033,595 B1
APPLICATION NO. : 09/762224
DATED : April 25, 2006
INVENTOR(S) : Sanders et al.

It is certified that error appears in the above-identified patent and that said Letters Patent is hereby corrected as shown below:

On The Title Page Item (75), under "Inventors" please delete "Scott A. Jeffers, West Lafayette, IN (US)".

On The Title Page Item (75), under "Inventors" please delete "Michael A. Fishbach, West Lafayette, IN (US)".

On page 2, column 2, please delete

"Taylor et al. "Fv-4: identification of the defect in Env and the mechanism of resistance to ecotropic murine leukemia virus. " *J Virol.* 2001;75(22):11244-8."

And insert:

-- Taylor et al. "Fv-4: identification of the defect in Env and the mechanism of resistance to ecotropic murine leukemia virus." *J Virol.* 2001;75(22):11244-8.--

Signed and Sealed this

Eighteenth Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,033,595 B1 | Page 1 of 1 |
| APPLICATION NO. | : 09/762224 | |
| DATED | : April 25, 2006 | |
| INVENTOR(S) | : Sanders et al. | |

It is certified that error appears in the above-identified patent and that said Letters Patent is hereby corrected as shown below:

Col. 44 lines 31-33

Please cancel claim 11.

Col. 45 lines 1-3

Please cancel claim 16.

Signed and Sealed this

Ninth Day of February, 2010

David J. Kappos
*Director of the United States Patent and Trademark Office*